United States Patent
Sikora et al.

(10) Patent No.: US 10,624,752 B2
(45) Date of Patent: Apr. 21, 2020

(54) TIBIAL RESURFACING SYSTEM AND METHOD

(71) Applicant: Arthrosurface, Inc., Franklin, MA (US)

(72) Inventors: George Sikora, Bridgewater, MA (US); Steven W. Ek, Bolton, MA (US)

(73) Assignee: Arthrosurface Incorporated, Franklin, MA (US)

( * ) Notice: Subject to any disclaimer, the term of this patent is extended or adjusted under 35 U.S.C. 154(b) by 0 days.

(21) Appl. No.: 14/133,943

(22) Filed: Dec. 19, 2013

(65) Prior Publication Data

US 2014/0155902 A1  Jun. 5, 2014

Related U.S. Application Data

(60) Division of application No. 13/042,382, filed on Mar. 7, 2011, now abandoned, which is a
(Continued)

(51) Int. Cl.
*A61F 2/38* (2006.01)
*A61B 17/15* (2006.01)
(Continued)

(52) U.S. Cl.
CPC ............ *A61F 2/389* (2013.01); *A61B 17/157* (2013.01); *A61B 17/1637* (2013.01);
(Continued)

(58) Field of Classification Search
CPC .. A61F 2002/30878; A61F 2002/30879; A61F 2002/30889–30892;
(Continued)

(56) References Cited

U.S. PATENT DOCUMENTS

| 103,645 A | 5/1870 | Muscroft |
| 992,819 A | 5/1911 | Springer |

(Continued)

FOREIGN PATENT DOCUMENTS

| AU | 2001262308 | 12/2001 |
| AU | 2001259327 B2 | 2/2005 |

(Continued)

OTHER PUBLICATIONS

"Cylinder." Merriam-Webster.com. Merriam-Webster, n. d. Web. Sep. 12, 2018. (Year: 2018).*

(Continued)

*Primary Examiner* — Jacqueline T Johanas
(74) *Attorney, Agent, or Firm* — Grossman Tucker Perreault & Pfleger PLLC

(57) ABSTRACT

An implant resection system for preparing an implant site to replace a defect in an articular surface of a first bone includes a guide configured to be coupled generally perpendicular to the first bone proximate to the defect. The guide includes a body portion defining a plurality of excision passageways. The excision passageways each define a generally cylindrical core pathway configured to extend generally perpendicular to the first bone which partially overlaps with an adjacent generally cylindrical core pathway. A projection associated with each of the plurality of the generally cylindrical core pathways defines a truncated cylindrical excision site extending through a portion of the articular surface. Each truncated cylindrical excision site partially overlaps with at least one adjacent truncated cylindrical excision site.

21 Claims, 16 Drawing Sheets

Related U.S. Application Data continuation-in-part of application No. 11/779,044, filed on Jul. 17, 2007, now abandoned.

(60) Provisional application No. 61/310,774, filed on Mar. 5, 2010, provisional application No. 60/807,538, filed on Jul. 17, 2006.

(51) Int. Cl.
    *A61B 17/16* (2006.01)
    *A61B 17/17* (2006.01)
    *A61B 90/00* (2016.01)

(52) U.S. Cl.
    CPC ...... *A61B 17/1675* (2013.01); *A61B 17/1764* (2013.01); *A61B 2090/062* (2016.02)

(58) Field of Classification Search
    CPC .................. A61F 2002/30899–30902; A61F 2002/30884; A61F 2002/30904; A61F 2/389; A61F 2/3868; A61F 2/3872
    See application file for complete search history.

(56) References Cited

U.S. PATENT DOCUMENTS

| | | |
|---|---|---|
| 1,451,610 A | 4/1923 | Gestas |
| 2,267,925 A | 12/1941 | Johnston |
| 2,379,984 A | 7/1943 | Nereaux |
| 2,381,102 A | 10/1943 | Boyd |
| 2,570,465 A | 10/1951 | Lundholm |
| 2,919,692 A | 1/1960 | Ackermann |
| 3,176,395 A | 4/1965 | Warner et al. |
| 3,351,115 A | 11/1967 | Boehlow |
| 3,715,763 A | 2/1973 | Link |
| 3,840,905 A | 10/1974 | Deane |
| 3,852,830 A | 12/1974 | Marmor |
| 4,016,651 A | 4/1977 | Kawahara et al. |
| 4,016,874 A | 4/1977 | Maffei et al. |
| 4,034,418 A | 7/1977 | Jackson et al. |
| D245,259 S * | 8/1977 | Shen .......................... D24/155 |
| 4,044,464 A | 8/1977 | Schiess et al. |
| 4,158,894 A | 6/1979 | Worrell |
| 4,304,011 A | 12/1981 | Whelan, III |
| 4,309,778 A * | 1/1982 | Buechel et al. ........... 623/20.29 |
| 4,319,577 A | 3/1982 | Bofinger et al. |
| 4,330,891 A | 5/1982 | Brånemark et al. |
| 4,340,978 A | 7/1982 | Buechel et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,565,768 A | 1/1986 | Nonogaki et al. |
| 4,567,885 A | 2/1986 | Androphy |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,703,761 A | 11/1987 | Rathbone et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A | 2/1988 | Fox |
| 4,729,761 A | 3/1988 | White |
| 4,743,262 A | 5/1988 | Tronzo |
| 4,778,473 A | 10/1988 | Matthews et al. |
| 4,781,182 A | 11/1988 | Purnell et al. |
| 4,787,383 A | 11/1988 | Kenna |
| 4,788,970 A | 12/1988 | Kara et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,919,671 A | 4/1990 | Karpf |
| 4,920,958 A | 5/1990 | Walt et al. |
| 4,927,421 A | 5/1990 | Goble et al. |
| 4,936,853 A | 6/1990 | Fabian et al. |
| 4,938,778 A | 7/1990 | Ohyabu et al. |
| 4,940,467 A | 7/1990 | Tronzo |
| 4,945,904 A | 8/1990 | Bolton et al. |
| 4,955,916 A | 9/1990 | Carignan et al. |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,030,219 A | 7/1991 | Matsen, III et al. |
| 5,053,049 A | 10/1991 | Campbell |
| 5,092,895 A | 3/1992 | Albrektsson et al. |
| 5,100,405 A | 3/1992 | McLaren |
| 5,122,144 A | 6/1992 | Bert et al. |
| 5,127,413 A | 7/1992 | Ebert |
| 5,127,920 A | 7/1992 | MacArthur |
| 5,147,386 A | 9/1992 | Carignan et al. |
| 5,152,797 A * | 10/1992 | Luckman et al. ......... 623/20.16 |
| 5,154,720 A | 10/1992 | Trott et al. |
| 5,180,384 A | 1/1993 | Mikhail |
| 5,192,291 A | 3/1993 | Pannek, Jr. |
| 5,194,066 A | 3/1993 | Van Zile |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,254,119 A | 10/1993 | Schreiber |
| 5,255,838 A | 10/1993 | Gladdish, Jr. et al. |
| 5,263,498 A | 11/1993 | Caspari et al. |
| 5,263,987 A | 11/1993 | Shah |
| 5,269,784 A | 12/1993 | Mast |
| 5,282,863 A | 2/1994 | Burton |
| 5,290,313 A | 3/1994 | Heldreth |
| 5,306,278 A | 4/1994 | Dahl et al. |
| 5,312,411 A | 5/1994 | Steele |
| 5,314,478 A | 5/1994 | Oka et al. |
| 5,314,482 A | 5/1994 | Goodfellow et al. |
| 5,324,295 A | 6/1994 | Shapiro |
| 5,326,366 A | 7/1994 | Pascarella et al. |
| 5,336,224 A | 8/1994 | Selman |
| 5,336,266 A * | 8/1994 | Caspari et al. ............ 623/20.35 |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,376 A | 3/1995 | Caspari et al. |
| 5,395,401 A | 3/1995 | Bahler |
| 5,409,490 A | 4/1995 | Ethridge |
| 5,409,494 A | 4/1995 | Morgan |
| 5,411,504 A | 5/1995 | Vilas |
| 5,413,608 A | 5/1995 | Keller |
| 5,423,822 A | 6/1995 | Hershberger |
| 5,423,823 A | 6/1995 | Schmieding |
| 5,425,733 A | 6/1995 | Schmieding |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,514,139 A | 5/1996 | Goldstein et al. |
| 5,520,695 A | 5/1996 | Luckman |
| 5,522,900 A | 6/1996 | Hollister |
| 5,522,901 A | 6/1996 | Thomas et al. |

(56) References Cited

U.S. PATENT DOCUMENTS

| | | |
|---|---|---|
| 5,534,031 A | 7/1996 | Matsuzaki et al. |
| 5,540,696 A | 7/1996 | Booth, Jr. et al. |
| 5,562,664 A | 10/1996 | Durlacher et al. |
| 5,580,352 A | 12/1996 | Sekel |
| 5,580,353 A | 12/1996 | Mendes et al. |
| 5,591,170 A | 1/1997 | Spievack et al. |
| 5,593,448 A | 1/1997 | Dong |
| 5,593,450 A | 1/1997 | Scott et al. |
| 5,595,193 A | 1/1997 | Walus et al. |
| 5,597,273 A | 1/1997 | Hirsch |
| 5,601,550 A | 2/1997 | Esser |
| 5,607,480 A | 3/1997 | Beaty |
| 5,609,639 A | 3/1997 | Walker |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,461 A | 12/1997 | Pappas et al. |
| 5,702,465 A | 12/1997 | Burkinshaw |
| 5,702,467 A | 12/1997 | Gabriel et al. |
| 5,720,753 A | 2/1998 | Sander et al. |
| 5,741,266 A | 4/1998 | Moran et al. |
| 5,765,973 A | 6/1998 | Hirsch et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,800,440 A | 9/1998 | Stead |
| 5,810,851 A | 9/1998 | Yoon |
| 5,816,811 A | 10/1998 | Beaty |
| 5,817,095 A | 10/1998 | Smith |
| 5,824,087 A | 10/1998 | Aspden et al. |
| 5,824,105 A | 10/1998 | Ries et al. |
| 5,827,285 A | 10/1998 | Bramlet |
| RE36,020 E | 12/1998 | Moore et al. |
| 5,871,545 A | 2/1999 | Goodfellow et al. |
| 5,879,396 A | 3/1999 | Walston et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,891,150 A | 4/1999 | Chan |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,241 A | 7/1999 | Menut et al. |
| 5,928,286 A | 7/1999 | Ashby et al. |
| 5,951,603 A | 9/1999 | O'Neil et al. |
| 5,957,979 A | 9/1999 | Beckman et al. |
| 5,964,752 A | 10/1999 | Stone |
| 5,964,768 A | 10/1999 | Huebner |
| 5,964,805 A | 10/1999 | Stone |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,019,790 A | 2/2000 | Holmberg et al. |
| 6,033,410 A | 3/2000 | McLean et al. |
| 6,045,554 A | 4/2000 | Grooms et al. |
| 6,045,564 A | 4/2000 | Walen |
| 6,052,909 A | 4/2000 | Gardner |
| 6,053,945 A | 4/2000 | O'Neil et al. |
| 6,059,831 A | 5/2000 | Braslow |
| 6,063,091 A | 5/2000 | Lombardo et al. |
| 6,069,295 A | 5/2000 | Leitao |
| 6,071,310 A | 6/2000 | Picha et al. |
| 6,081,741 A | 6/2000 | Hollis |
| 6,086,593 A | 7/2000 | Bonutti |
| 6,086,614 A | 7/2000 | Mumme |
| 6,099,571 A | 8/2000 | Knapp |
| 6,102,948 A | 8/2000 | Brosnahan, III |
| 6,102,954 A * | 8/2000 | Albrektsson et al. ..... 623/20.32 |
| 6,120,511 A | 9/2000 | Chan |
| 6,120,542 A | 9/2000 | Camino et al. |
| 6,132,433 A | 10/2000 | Whelan |
| 6,139,508 A | 10/2000 | Simpson et al. |
| 6,146,385 A | 11/2000 | Torrie et al. |
| 6,149,654 A | 11/2000 | Lanny |
| 6,152,960 A | 11/2000 | Pappas |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,206,926 B1 | 3/2001 | Pappas |
| 6,207,218 B1 | 3/2001 | Layrolle et al. |
| 6,217,549 B1 | 4/2001 | Selmon et al. |
| 6,217,619 B1 | 4/2001 | Keller |
| 6,228,119 B1 | 5/2001 | Ondrla et al. |
| 6,231,611 B1 | 5/2001 | Mosseri |
| 6,235,060 B1 | 5/2001 | Kubein-Meesenburg et al. |
| 6,245,074 B1 | 6/2001 | Allard et al. |
| 6,251,143 B1 | 6/2001 | Schwartz et al. |
| 6,254,605 B1 | 7/2001 | Howell |
| 6,270,347 B1 | 8/2001 | Webster et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,310,116 B1 | 10/2001 | Yasuda et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,364,910 B1 | 4/2002 | Shultz et al. |
| 6,375,658 B1 | 4/2002 | Hangody et al. |
| 6,383,188 B2 | 5/2002 | Kuslich |
| 6,402,785 B1 * | 6/2002 | Zdeblick et al. .......... 623/17.16 |
| 6,415,516 B1 | 7/2002 | Tirado et al. |
| 6,416,518 B1 | 7/2002 | DeMayo |
| 6,443,954 B1 | 9/2002 | Bramlet et al. |
| 6,451,023 B1 | 9/2002 | Salazar et al. |
| 6,461,373 B2 | 10/2002 | Wyman et al. |
| 6,468,309 B1 | 10/2002 | Lieberman |
| 6,478,801 B1 | 11/2002 | Ralph et al. |
| 6,478,822 B1 | 11/2002 | Leroux et al. |
| 6,482,210 B1 | 11/2002 | Skiba et al. |
| 6,494,914 B2 | 12/2002 | Brown |
| 6,517,541 B1 | 2/2003 | Sesic |
| 6,517,542 B1 | 2/2003 | Papay et al. |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,547,823 B2 * | 4/2003 | Scarborough et al. .... 623/17.16 |
| 6,551,322 B1 | 4/2003 | Lieberman |
| 6,554,866 B1 | 4/2003 | Aicher et al. |
| 6,558,422 B1 | 5/2003 | Baker et al. |
| 6,569,202 B2 | 5/2003 | Whiteside |

(56) References Cited

U.S. PATENT DOCUMENTS

| | | | |
|---|---|---|---|
| 6,575,980 B1 | 6/2003 | Robie et al. |
| 6,575,982 B1 | 6/2003 | Bonutti |
| 6,585,666 B2 | 7/2003 | Suh et al. |
| 6,589,281 B2 | 7/2003 | Hyde, Jr. |
| 6,591,581 B2 | 7/2003 | Schmieding |
| 6,599,321 B2 | 7/2003 | Hyde et al. |
| 6,602,258 B1 | 8/2003 | Katz |
| 6,607,561 B2 | 8/2003 | Brannon |
| 6,610,067 B2 | 8/2003 | Tallarida |
| 6,610,095 B1 | 8/2003 | Pope et al. |
| 6,623,474 B1 | 9/2003 | Ponzi |
| 6,626,950 B2 | 9/2003 | Brown et al. |
| 6,629,997 B2 | 10/2003 | Mansmann |
| 6,632,246 B1 | 10/2003 | Simon et al. |
| 6,679,916 B1 | 1/2004 | Frankle et al. |
| 6,679,917 B2 | 1/2004 | Ek |
| 6,720,469 B1 | 4/2004 | Curtis et al. |
| 6,746,451 B2 | 6/2004 | Middleton et al. |
| 6,755,837 B2 | 6/2004 | Ebner |
| 6,755,865 B2 | 6/2004 | Tarabishy |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,881,228 B2 * | 4/2005 | Zdeblick et al. .......... 623/17.16 |
| 6,884,246 B1 | 4/2005 | Sonnabend et al. |
| 6,884,621 B2 | 4/2005 | Liao et al. |
| 6,893,467 B1 | 5/2005 | Bercovy |
| 6,913,463 B2 | 7/2005 | Blacklock |
| 6,923,813 B2 | 8/2005 | Phillips et al. |
| 6,926,739 B1 | 8/2005 | Oconnor |
| 6,951,538 B2 | 10/2005 | Ritland |
| 6,953,478 B2 | 10/2005 | Bouttens et al. |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,048,767 B2 | 5/2006 | Namavar |
| 7,063,717 B2 | 6/2006 | St. Pierre et al. |
| 7,112,205 B2 | 9/2006 | Carrison |
| 7,115,131 B2 | 10/2006 | Engh et al. |
| 7,118,578 B2 | 10/2006 | West, Jr. et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,192,432 B2 | 3/2007 | Wetzler et al. |
| 7,204,839 B2 | 4/2007 | Dreyfuss et al. |
| 7,204,854 B2 | 4/2007 | Guederian et al. |
| 7,229,448 B2 | 6/2007 | Goble et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augustino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,368,065 B2 | 5/2008 | Yang et al. |
| 7,371,260 B2 | 5/2008 | Malinin |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,575,578 B2 | 8/2009 | Wetzler et al. |
| 7,578,824 B2 | 8/2009 | Justin et al. |
| 7,604,641 B2 | 10/2009 | Tallarida et al. |
| 7,611,653 B1 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,731,738 B2 | 6/2010 | Jackson et al. |
| 7,738,187 B2 | 6/2010 | Pazidis et al. |
| 7,740,662 B2 | 6/2010 | Barnett et al. |
| 7,758,643 B2 | 7/2010 | Stone et al. |
| 7,776,085 B2 | 8/2010 | Bernero et al. |
| 7,806,872 B2 | 10/2010 | Ponzi |
| 7,815,645 B2 | 10/2010 | Haines |
| 7,815,681 B2 | 10/2010 | Ferguson |
| 7,828,853 B2 | 11/2010 | Ek et al. |
| 7,842,042 B2 | 11/2010 | Reay-Young et al. |
| 7,857,817 B2 | 12/2010 | Tallarida et al. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,914,545 B2 | 3/2011 | Ek |
| 7,931,683 B2 | 4/2011 | Weber et al. |
| 7,951,163 B2 | 5/2011 | Ek |
| 7,951,204 B2 | 5/2011 | Chambat et al. |
| 7,955,382 B2 | 6/2011 | Flanagan et al. |
| 7,959,636 B2 | 6/2011 | Schmieding |
| 7,959,650 B2 | 6/2011 | Kaiser et al. |
| 7,959,681 B2 | 6/2011 | Lavi |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,114,163 B2 | 2/2012 | Berelsman et al. |
| 8,137,406 B2 | 3/2012 | Novak et al. |
| 8,137,407 B2 | 3/2012 | Todd et al. |
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,157,867 B2 | 4/2012 | Goble et al. |
| 8,162,947 B2 | 4/2012 | Dreyfuss |
| 8,163,027 B2 * | 4/2012 | Rhodes et al. ............. 623/20.34 |
| 8,167,951 B2 | 5/2012 | Ammann et al. |
| 8,177,738 B2 | 5/2012 | Schmieding et al. |
| 8,177,841 B2 | 5/2012 | Ek |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas et al. |

(56) References Cited

U.S. PATENT DOCUMENTS

| | | |
|---|---|---|
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,267,977 B2 | 9/2012 | Roth |
| 8,298,247 B2 | 10/2012 | Sterrett et al. |
| 8,298,284 B2 | 10/2012 | Cassani |
| 8,303,830 B2 | 11/2012 | Tong et al. |
| 8,308,662 B2 | 11/2012 | Lo |
| 8,308,732 B2 | 11/2012 | Millett et al. |
| 8,308,781 B2 | 11/2012 | Wilson et al. |
| 8,317,870 B2 | 11/2012 | Wagner et al. |
| 8,323,347 B2 | 12/2012 | Guederian et al. |
| 8,328,716 B2 | 12/2012 | Schmieding et al. |
| 8,333,774 B2 | 12/2012 | Morrison |
| 8,343,186 B2 | 1/2013 | Dreyfuss et al. |
| 8,348,960 B2 | 1/2013 | Michel et al. |
| 8,348,975 B2 | 1/2013 | Dreyfuss |
| 8,353,915 B2 | 1/2013 | Helenbolt et al. |
| 8,361,159 B2 | 1/2013 | Ek |
| 8,377,068 B2 | 2/2013 | Aker et al. |
| 8,382,789 B2 | 2/2013 | Weber et al. |
| 8,382,810 B2 | 2/2013 | Peterson et al. |
| 8,388,624 B2 | 3/2013 | Ek et al. |
| 8,398,678 B2 | 3/2013 | Baker et al. |
| 8,409,209 B2 | 4/2013 | Ammann et al. |
| 8,409,250 B2 | 4/2013 | Schmieding et al. |
| 8,414,908 B2 | 4/2013 | Jin et al. |
| 8,419,794 B2 | 4/2013 | ElAttrache et al. |
| 8,425,554 B2 | 4/2013 | Denove et al. |
| 8,430,909 B2 | 4/2013 | Dreyfuss |
| 8,435,272 B2 | 5/2013 | Dougherty et al. |
| 8,439,976 B2 | 5/2013 | Albertorio et al. |
| 8,444,680 B2 | 5/2013 | Dooney, Jr. et al. |
| 8,460,317 B2 | 6/2013 | Merves |
| 8,460,318 B2 | 6/2013 | Murray et al. |
| 8,460,350 B2 | 6/2013 | Albertorio et al. |
| 8,460,379 B2 | 6/2013 | Albertorio et al. |
| 8,470,047 B2 | 6/2013 | Hazebrouck et al. |
| 8,475,536 B2 | 7/2013 | Tong et al. |
| 8,486,072 B2 | 7/2013 | Haininger |
| 8,496,662 B2 | 7/2013 | Novak et al. |
| 8,506,573 B2 | 8/2013 | Dreyfuss et al. |
| 8,512,376 B2 | 8/2013 | Thornes |
| 8,512,411 B2 | 8/2013 | Sluss et al. |
| 8,523,872 B2 | 9/2013 | Ek |
| 8,535,330 B2 | 9/2013 | Sherman et al. |
| 8,535,703 B2 | 9/2013 | Schmieding et al. |
| 8,540,717 B2 | 9/2013 | Tallarida et al. |
| 8,540,777 B2 | 9/2013 | Ammann et al. |
| 8,540,778 B2 * | 9/2013 | Rhodes et al. ............ 623/20.34 |
| 8,551,101 B2 | 10/2013 | Kuczynski |
| 8,579,940 B2 | 11/2013 | Dreyfuss et al. |
| 8,579,944 B2 | 11/2013 | Holloway et al. |
| 8,591,514 B2 | 11/2013 | Sherman |
| 8,591,523 B2 | 11/2013 | Weber |
| 8,591,544 B2 | 11/2013 | Jolly et al. |
| 8,591,578 B2 | 11/2013 | Albertorio et al. |
| 8,591,592 B2 | 11/2013 | Dreyfuss |
| 8,591,594 B2 | 11/2013 | Parisi et al. |
| 8,597,361 B2 * | 12/2013 | Sidebotham et al. ...... 623/18.11 |
| 8,623,052 B2 | 1/2014 | Dreyfuss et al. |
| 8,628,573 B2 | 1/2014 | Roller et al. |
| 8,652,139 B2 | 2/2014 | Sterrett et al. |
| 8,663,230 B2 | 3/2014 | Miniaci et al. |
| 8,663,250 B2 | 3/2014 | Weber |
| 8,663,251 B2 | 3/2014 | Burkhart et al. |
| 8,663,279 B2 | 3/2014 | Burkhart et al. |
| 8,663,324 B2 | 3/2014 | Schmieding et al. |
| 8,663,333 B2 | 3/2014 | Metcalfe et al. |
| 8,668,738 B2 | 3/2014 | Schmieding et al. |
| 8,702,715 B2 | 4/2014 | Ammann et al. |
| 8,702,752 B2 | 4/2014 | Schmieding et al. |
| 8,709,052 B2 | 4/2014 | Ammann et al. |
| 8,709,091 B2 * | 4/2014 | Rhodes et al. ............ 623/20.32 |
| 8,721,722 B2 * | 5/2014 | Shah et al. ................ 623/17.15 |
| 8,728,131 B2 | 5/2014 | Di Giacomo et al. |
| 8,734,449 B2 | 5/2014 | Schmied et al. |
| 8,753,375 B2 | 6/2014 | Albertorio |
| 8,758,356 B2 | 6/2014 | Fearon et al. |
| 8,764,797 B2 | 7/2014 | Dreyfuss et al. |
| 8,764,807 B2 | 7/2014 | Michel et al. |
| 8,764,839 B2 * | 7/2014 | Rhodes et al. ............ 623/20.32 |
| 8,771,279 B2 | 7/2014 | Philippon et al. |
| 8,771,351 B2 | 7/2014 | ElAttrache et al. |
| 8,784,423 B2 | 7/2014 | Kowarsch et al. |
| 8,790,401 B2 | 7/2014 | Schmieding et al. |
| 8,801,755 B2 | 8/2014 | Dreyfuss et al. |
| 8,821,541 B2 | 9/2014 | Dreyfuss et al. |
| 8,834,475 B2 | 9/2014 | Ammann et al. |
| 8,834,521 B2 | 9/2014 | Pinto et al. |
| 8,840,619 B2 | 9/2014 | Zajac et al. |
| 8,840,643 B2 | 9/2014 | Dreyfuss |
| 8,852,190 B2 | 10/2014 | Sherman |
| 8,852,201 B2 | 10/2014 | Schmieding et al. |
| 8,858,560 B2 | 10/2014 | Bradley et al. |
| 8,864,827 B2 | 10/2014 | Ek |
| 8,870,877 B2 | 10/2014 | Koogle, Jr. |
| 8,876,900 B2 | 11/2014 | Guederian et al. |
| 8,882,833 B2 | 11/2014 | Saylor et al. |
| 8,882,845 B2 | 11/2014 | Wirth et al. |
| 8,882,847 B2 | 11/2014 | Burdulis, Jr. et al. |
| 8,888,781 B2 | 11/2014 | Sterrett |
| 8,888,785 B2 | 11/2014 | Ammann et al. |
| 8,888,815 B2 | 11/2014 | Holmes, Jr. |
| 8,906,026 B2 | 12/2014 | Ammann et al. |
| 8,911,457 B2 | 12/2014 | Koogle, Jr. et al. |
| 8,920,497 B2 | 12/2014 | Albertorio et al. |
| 8,926,615 B2 | 1/2015 | Ek |
| 8,927,283 B2 | 1/2015 | Komvopoulos et al. |
| 8,939,980 B2 | 1/2015 | Schmieding et al. |
| 8,939,999 B2 | 1/2015 | Sterrett et al. |
| 8,956,369 B2 | 2/2015 | Millett et al. |
| 8,961,538 B2 | 2/2015 | Koogle, Jr. et al. |
| 8,961,575 B2 | 2/2015 | Choinski |
| 8,961,614 B2 | 2/2015 | Ek et al. |
| 8,974,537 B2 | 3/2015 | Dreyfuss |
| 8,986,346 B2 | 3/2015 | Dreyfuss |
| 9,005,245 B2 | 4/2015 | Thornes et al. |
| 9,005,246 B2 | 4/2015 | Burkhart et al. |
| 9,044,343 B2 | 6/2015 | Ek |
| 9,055,955 B2 | 6/2015 | Ek et al. |
| 9,066,716 B2 | 6/2015 | Sikora et al. |
| 9,072,510 B2 | 7/2015 | Thornes et al. |
| 9,072,555 B2 | 7/2015 | Michel |
| 9,078,650 B2 | 7/2015 | Weber |
| 9,078,661 B2 | 7/2015 | Gallo |
| 9,089,363 B2 | 7/2015 | Dooney, Jr. et al. |
| 9,089,433 B2 | 7/2015 | Karnes et al. |
| 9,095,641 B2 | 8/2015 | Albertorio |
| 9,101,366 B2 | 8/2015 | Sterrett et al. |
| 9,101,461 B2 | 8/2015 | Albertorio et al. |
| 9,107,653 B2 | 8/2015 | Sullivan |
| 9,107,676 B2 | 8/2015 | Burkhart et al. |
| 9,113,859 B2 | 8/2015 | Dooney, Jr. et al. |
| 9,113,920 B2 | 8/2015 | Ammann et al. |
| 9,138,223 B2 | 9/2015 | Jolly et al. |
| 9,138,237 B2 | 9/2015 | Meade et al. |
| 9,138,241 B2 | 9/2015 | Kuczynski |
| 9,138,246 B2 | 9/2015 | Anderson et al. |
| 9,138,274 B1 | 9/2015 | Biesinger et al. |
| 9,146,576 B2 | 9/2015 | Schmieding et al. |
| 9,168,124 B2 | 10/2015 | Guerra et al. |
| 9,179,907 B2 | 11/2015 | ElAttrache et al. |
| 9,179,950 B2 | 11/2015 | Zajac et al. |
| 9,186,432 B2 | 11/2015 | Mazzocca et al. |
| 9,204,873 B2 | 12/2015 | Tallarida et al. |
| 9,204,874 B2 | 12/2015 | Denove et al. |
| 9,204,960 B2 | 12/2015 | Albertorio et al. |
| 9,211,126 B2 | 12/2015 | Sikora et al. |
| 9,216,017 B2 | 12/2015 | Burkhart |
| 9,216,022 B2 | 12/2015 | Karnes et al. |
| 9,216,090 B2 | 12/2015 | Metcalfe |
| 9,216,091 B2 | 12/2015 | Hardy et al. |
| 9,226,743 B2 | 1/2016 | Dreyfuss et al. |

(56) References Cited

U.S. PATENT DOCUMENTS

| | | |
|---|---|---|
| 9,226,815 B2 | 1/2016 | Schmieding et al. |
| 9,283,076 B2 | 3/2016 | Sikora et al. |
| 9,295,556 B2 | 3/2016 | Perez, III et al. |
| 9,301,745 B2 | 4/2016 | Dreyfuss |
| 9,301,847 B2 | 4/2016 | Guederian et al. |
| 9,320,512 B2 | 4/2016 | Dooney, Jr. |
| 9,332,979 B2 | 5/2016 | Sullivan et al. |
| 9,333,019 B2 | 5/2016 | Khosla et al. |
| 9,345,471 B2 | 5/2016 | Sullivan |
| 9,351,722 B2 | 5/2016 | Koogle, Jr. et al. |
| 9,351,745 B2 | 5/2016 | Ek et al. |
| 9,357,989 B2 | 6/2016 | Tallarida et al. |
| 9,358,029 B2 | 6/2016 | Sikora et al. |
| 9,364,214 B2 | 6/2016 | Courage |
| 9,381,022 B2 | 7/2016 | Bradley et al. |
| 9,381,053 B2 | 7/2016 | Parsons et al. |
| 9,393,010 B2 | 7/2016 | Murray et al. |
| 9,402,730 B2 | 8/2016 | Lederman et al. |
| 9,421,007 B2 | 8/2016 | Brady et al. |
| 9,421,008 B2 | 8/2016 | Burkhart et al. |
| 9,421,010 B2 | 8/2016 | Dreyfuss |
| 9,421,086 B2 | 8/2016 | Roller et al. |
| 9,421,105 B2 | 8/2016 | Metcalfe et al. |
| 9,451,951 B2 | 9/2016 | Sullivan et al. |
| 9,463,011 B2 | 10/2016 | Dreyfuss et al. |
| 9,468,448 B2 | 10/2016 | Sikora et al. |
| 9,485,475 B2 | 11/2016 | Speier et al. |
| 9,486,207 B2 | 11/2016 | Dooney, Jr. et al. |
| 9,486,317 B2 | 11/2016 | Milano et al. |
| 9,492,200 B2 | 11/2016 | Sikora et al. |
| 9,498,232 B2 | 11/2016 | Perez, III |
| 9,504,462 B2 | 11/2016 | Dooney, Jr. et al. |
| 9,510,840 B2 | 12/2016 | Sikora et al. |
| 9,510,951 B2 | 12/2016 | Bachmaier |
| 9,521,999 B2 | 12/2016 | Dreyfuss et al. |
| 9,526,493 B2 | 12/2016 | Dreyfuss et al. |
| 9,526,510 B2 | 12/2016 | Sterrett |
| 9,549,701 B2 | 1/2017 | Peterson et al. |
| 9,549,726 B2 | 1/2017 | Dreyfuss et al. |
| 9,603,712 B2 | 3/2017 | Bachmaier |
| 9,610,167 B2 | 4/2017 | Hardy et al. |
| 9,615,821 B2 | 4/2017 | Sullivan |
| 9,622,738 B2 | 4/2017 | Dreyfuss et al. |
| 9,622,739 B2 | 4/2017 | Dreyfuss et al. |
| 9,622,775 B2 | 4/2017 | Jolly et al. |
| 9,642,609 B2 | 5/2017 | Holmes, Jr. |
| 9,642,610 B2 | 5/2017 | Albertorio et al. |
| 9,662,126 B2 | 5/2017 | Sikora et al. |
| 9,687,222 B2 | 6/2017 | Dreyfuss et al. |
| 9,687,256 B2 | 6/2017 | Granberry et al. |
| 9,687,338 B2 | 6/2017 | Albertorio et al. |
| 9,693,765 B2 | 7/2017 | Sullivan et al. |
| 9,693,787 B2 | 7/2017 | Ammann et al. |
| 9,706,986 B2 | 7/2017 | ElAttrache et al. |
| 9,707,023 B2 | 7/2017 | Ammann et al. |
| 9,724,138 B2 | 8/2017 | Palmer et al. |
| 9,737,292 B2 | 8/2017 | Sullivan et al. |
| 9,750,850 B2 | 9/2017 | Fonte et al. |
| 9,775,599 B2 | 10/2017 | Elattrache et al. |
| 9,795,392 B2 | 10/2017 | Zajac |
| 9,801,625 B2 | 10/2017 | Dooney, Jr. et al. |
| 9,801,707 B2 | 10/2017 | Cassani |
| 9,801,726 B2 | 10/2017 | Karnes et al. |
| 9,808,240 B2 | 11/2017 | Parsons et al. |
| 9,814,455 B2 | 11/2017 | Dooney, Jr. et al. |
| 9,814,499 B2 | 11/2017 | Buscaglia et al. |
| 9,833,260 B2 | 12/2017 | Jolly et al. |
| 9,839,462 B2 | 12/2017 | Zajac |
| 9,855,029 B2 | 1/2018 | Sullivan |
| 9,855,036 B2 | 1/2018 | Palmer et al. |
| 9,855,064 B2 | 1/2018 | Albertorio et al. |
| 9,855,132 B2 | 1/2018 | Hoover et al. |
| 9,855,146 B2 | 1/2018 | Schmieding |
| 9,861,357 B2 | 1/2018 | Palmer et al. |
| 9,861,413 B2 | 1/2018 | Palmer et al. |
| 9,861,417 B2 | 1/2018 | Helenbolt et al. |
| 9,861,492 B2 | 1/2018 | Ek |
| 9,867,607 B2 | 1/2018 | Sullivan |
| 9,877,712 B2 | 1/2018 | Provencher et al. |
| 9,877,758 B2 | 1/2018 | Michel |
| 9,888,997 B2 | 2/2018 | Dreyfuss et al. |
| 9,895,177 B2 | 2/2018 | Hientzsch et al. |
| 9,907,655 B2 | 3/2018 | Ingwer et al. |
| 9,907,657 B2 | 3/2018 | Fonte et al. |
| 9,913,640 B2 | 3/2018 | Perez, III |
| 9,918,769 B2 | 3/2018 | Provencher et al. |
| 9,931,115 B2 | 4/2018 | Morgan et al. |
| 9,931,211 B2 | 4/2018 | Ek et al. |
| 9,931,219 B2 | 4/2018 | Sikora et al. |
| 9,962,265 B2 | 5/2018 | Ek et al. |
| 9,974,537 B2 | 5/2018 | Coughlin et al. |
| 9,974,550 B2 | 5/2018 | Seitlinger et al. |
| 9,999,416 B2 | 6/2018 | Kelly et al. |
| 10,045,770 B2 | 8/2018 | Burkhart et al. |
| 10,045,788 B2 | 8/2018 | Sikora et al. |
| 10,052,091 B2 | 8/2018 | Dreyfuss et al. |
| 10,058,322 B2 | 8/2018 | Dooney, Jr. et al. |
| 10,064,983 B2 | 8/2018 | Weber et al. |
| 10,076,321 B2 | 9/2018 | Crane et al. |
| 10,076,322 B1 | 9/2018 | Dreyfuss |
| 10,076,343 B2 | 9/2018 | Ek |
| 10,076,407 B2 | 9/2018 | Albertorio et al. |
| 10,080,557 B1 | 9/2018 | Laviano et al. |
| 10,085,739 B2 | 10/2018 | Dooney, Jr. et al. |
| 10,092,340 B2 | 10/2018 | Choinski et al. |
| 10,111,649 B2 | 10/2018 | Laviano et al. |
| 10,117,657 B2 | 11/2018 | Guederian |
| 10,159,518 B2 | 12/2018 | Holowecky et al. |
| 10,172,606 B2 | 1/2019 | Sullivan et al. |
| 10,172,607 B2 | 1/2019 | Burkhart |
| 10,172,703 B2 | 1/2019 | Adams et al. |
| 10,182,917 B2 | 1/2019 | Zajac |
| 10,188,504 B2 | 1/2019 | Cassani |
| 10,194,899 B2 | 2/2019 | Benavitz et al. |
| 10,206,670 B2 | 2/2019 | Thornes |
| 10,206,694 B2 | 2/2019 | Libby et al. |
| 10,213,219 B2 | 2/2019 | Garlock et al. |
| 10,238,484 B2 | 3/2019 | Albertorio et al. |
| 10,245,016 B2 | 4/2019 | Zajac et al. |
| 10,251,655 B2 | 4/2019 | Sterrett |
| 10,251,656 B2 | 4/2019 | Granberry et al. |
| 10,251,686 B2 | 4/2019 | Zajac et al. |
| 10,258,320 B2 | 4/2019 | Dreyfuss et al. |
| 10,265,060 B2 | 4/2019 | Dooney, Jr. et al. |
| 10,285,801 B2 | 5/2019 | Roller et al. |
| 10,299,841 B2 | 5/2019 | Dunlop et al. |
| 10,307,154 B2 | 6/2019 | Michalik et al. |
| 10,363,024 B2 | 7/2019 | Koogle, Jr. et al. |
| 10,398,426 B2 | 9/2019 | Burkhart et al. |
| 10,405,904 B2 | 9/2019 | Hientzsch et al. |
| 10,413,341 B2 | 9/2019 | Chaudot et al. |
| 10,420,597 B2 | 9/2019 | Papangelou et al. |
| 10,448,945 B2 | 10/2019 | Bachmaier et al. |
| 10,456,145 B2 | 10/2019 | Laviano et al. |
| 10,478,200 B2 | 11/2019 | Sikora et al. |
| 10,499,932 B2 | 12/2019 | Koogle, Jr. et al. |
| 10,512,543 B2 | 12/2019 | Ingwer et al. |
| 2001/0010023 A1 | 7/2001 | Schwartz et al. |
| 2001/0012967 A1 | 8/2001 | Mosseri |
| 2001/0016775 A1* | 8/2001 | Scarborough et al. .... 623/17.16 |
| 2001/0034526 A1 | 10/2001 | Kuslich et al. |
| 2001/0039455 A1 | 11/2001 | Simon et al. |
| 2001/0053914 A1 | 12/2001 | Landry et al. |
| 2001/0056266 A1 | 12/2001 | Tallarida et al. |
| 2002/0022847 A1 | 2/2002 | Ray, III et al. |
| 2002/0022889 A1 | 2/2002 | Chibrac et al. |
| 2002/0022890 A1* | 2/2002 | Jacobsson et al. ........ 623/18.11 |
| 2002/0049444 A1 | 4/2002 | Knox |
| 2002/0055783 A1 | 5/2002 | Tallarida et al. |
| 2002/0082701 A1* | 6/2002 | Zdeblick et al. .......... 623/17.16 |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |

(56) References Cited

U.S. PATENT DOCUMENTS

| | | | |
|---|---|---|---|
| 2002/0155144 A1 | 10/2002 | Troczynski et al. | |
| 2002/0156480 A1 | 10/2002 | Overes et al. | |
| 2002/0173797 A1 | 11/2002 | Van Zile et al. | |
| 2002/0183760 A1 | 12/2002 | McGovern et al. | |
| 2003/0028196 A1 | 2/2003 | Bonutti | |
| 2003/0060887 A1 | 3/2003 | Ek | |
| 2003/0065332 A1 | 4/2003 | TenHuisen et al. | |
| 2003/0065391 A1 | 4/2003 | Re et al. | |
| 2003/0083751 A1 | 5/2003 | Tornier | |
| 2003/0100953 A1 | 5/2003 | Rosa et al. | |
| 2003/0105465 A1 | 6/2003 | Schmieding et al. | |
| 2003/0120276 A1 | 6/2003 | Tallarida et al. | |
| 2003/0120278 A1 | 6/2003 | Morgan et al. | |
| 2003/0130741 A1 | 7/2003 | McMinn | |
| 2003/0144736 A1 | 7/2003 | Sennett | |
| 2003/0171756 A1 | 9/2003 | Fallin et al. | |
| 2003/0171820 A1 | 9/2003 | Wilshaw et al. | |
| 2003/0181878 A1 | 9/2003 | Tallarida et al. | |
| 2003/0195470 A1 | 10/2003 | Ponzi | |
| 2003/0204195 A1 | 10/2003 | Keane et al. | |
| 2003/0204267 A1 | 10/2003 | Hazebrouck et al. | |
| 2003/0216669 A1 | 11/2003 | Lang et al. | |
| 2003/0216742 A1 | 11/2003 | Wetzler et al. | |
| 2003/0225456 A1 | 12/2003 | Ek | |
| 2003/0225457 A1 | 12/2003 | Justin et al. | |
| 2003/0229352 A1 | 12/2003 | Penenberg | |
| 2004/0015170 A1 | 1/2004 | Tallarida et al. | |
| 2004/0033212 A1 | 2/2004 | Thomson et al. | |
| 2004/0034359 A1 | 2/2004 | Schmieding et al. | |
| 2004/0034437 A1 | 2/2004 | Schmieding | |
| 2004/0039389 A1 | 2/2004 | West, Jr. et al. | |
| 2004/0064190 A1 | 4/2004 | Ball et al. | |
| 2004/0082906 A1 | 4/2004 | Tallarida et al. | |
| 2004/0083005 A1* | 4/2004 | Jacobsson et al. | 623/23.44 |
| 2004/0092946 A1 | 5/2004 | Bagga et al. | |
| 2004/0106928 A1 | 6/2004 | Ek | |
| 2004/0133276 A1 | 7/2004 | Lang et al. | |
| 2004/0138754 A1 | 7/2004 | Lang et al. | |
| 2004/0138758 A1 | 7/2004 | Evans et al. | |
| 2004/0148030 A1 | 7/2004 | Ek | |
| 2004/0153086 A1 | 8/2004 | Sanford | |
| 2004/0153087 A1 | 8/2004 | Sanford et al. | |
| 2004/0167632 A1 | 8/2004 | Wen et al. | |
| 2004/0167633 A1 | 8/2004 | Wen et al. | |
| 2004/0176775 A1 | 9/2004 | Burkus et al. | |
| 2004/0186582 A1* | 9/2004 | Yasuda et al. | 623/20.21 |
| 2004/0193172 A1 | 9/2004 | Ross et al. | |
| 2004/0193175 A1 | 9/2004 | Maroney et al. | |
| 2004/0193267 A1 | 9/2004 | Jones et al. | |
| 2004/0193268 A1 | 9/2004 | Hazebrouck | |
| 2004/0193281 A1 | 9/2004 | Grimes | |
| 2004/0199166 A1 | 10/2004 | Schmieding et al. | |
| 2004/0204760 A1 | 10/2004 | Fitz et al. | |
| 2004/0210309 A1 | 10/2004 | Denzer et al. | |
| 2004/0220574 A1 | 11/2004 | Pelo et al. | |
| 2004/0230315 A1 | 11/2004 | Ek | |
| 2004/0236339 A1 | 11/2004 | Pepper | |
| 2004/0254585 A1 | 12/2004 | Whittaker et al. | |
| 2004/0260303 A1 | 12/2004 | Carrison | |
| 2005/0015092 A1 | 1/2005 | Rathbun et al. | |
| 2005/0015153 A1 | 1/2005 | Gobel et al. | |
| 2005/0038520 A1 | 2/2005 | Binette et al. | |
| 2005/0043805 A1 | 2/2005 | Chudik | |
| 2005/0043808 A1 | 2/2005 | Felt et al. | |
| 2005/0049716 A1 | 3/2005 | Wagener et al. | |
| 2005/0065612 A1 | 3/2005 | Winslow | |
| 2005/0071014 A1 | 3/2005 | Barnett et al. | |
| 2005/0075642 A1 | 4/2005 | Felt | |
| 2005/0085909 A1* | 4/2005 | Eisermann | 623/17.11 |
| 2005/0090905 A1 | 4/2005 | Hawkins et al. | |
| 2005/0107799 A1 | 5/2005 | Graf et al. | |
| 2005/0119758 A1 | 6/2005 | Alexander et al. | |
| 2005/0143731 A1 | 6/2005 | Justin et al. | |
| 2005/0143745 A1 | 6/2005 | Hodorek et al. | |
| 2005/0143821 A1* | 6/2005 | Zdeblick et al. | 623/17.11 |
| 2005/0143831 A1 | 6/2005 | Justin et al. | |
| 2005/0149044 A1 | 7/2005 | Justin et al. | |
| 2005/0154398 A1 | 7/2005 | Miniaci et al. | |
| 2005/0165407 A1 | 7/2005 | Diaz | |
| 2005/0165487 A1* | 7/2005 | Muhanna et al. | 623/17.15 |
| 2005/0177171 A1 | 8/2005 | Wetzler et al. | |
| 2005/0209705 A1 | 9/2005 | Niederauer et al. | |
| 2005/0222687 A1 | 10/2005 | Vunjak-Novakovic et al. | |
| 2005/0229323 A1 | 10/2005 | Mills et al. | |
| 2005/0234461 A1 | 10/2005 | Burdulis, Jr. et al. | |
| 2005/0245932 A1 | 11/2005 | Fanton et al. | |
| 2005/0251268 A1 | 11/2005 | Truncale | |
| 2005/0273112 A1 | 12/2005 | McNamara | |
| 2005/0287187 A1 | 12/2005 | Mansmann | |
| 2006/0004461 A1 | 1/2006 | Justin et al. | |
| 2006/0009774 A1 | 1/2006 | Goble et al. | |
| 2006/0020343 A1 | 1/2006 | Ek | |
| 2006/0041261 A1 | 2/2006 | Osypka | |
| 2006/0052878 A1 | 3/2006 | Schmieding | |
| 2006/0058744 A1 | 3/2006 | Tallarida et al. | |
| 2006/0058809 A1 | 3/2006 | Zink et al. | |
| 2006/0058883 A1 | 3/2006 | Aram et al. | |
| 2006/0069394 A1 | 3/2006 | Weiler et al. | |
| 2006/0074430 A1 | 4/2006 | Deffenbaugh et al. | |
| 2006/0085006 A1 | 4/2006 | Ek | |
| 2006/0085077 A1 | 4/2006 | Cook et al. | |
| 2006/0105015 A1 | 5/2006 | Perla et al. | |
| 2006/0111787 A1* | 5/2006 | Bailie et al. | 623/19.13 |
| 2006/0121080 A1 | 6/2006 | Lye et al. | |
| 2006/0142772 A1 | 6/2006 | Ralph et al. | |
| 2006/0149370 A1 | 7/2006 | Schmieding et al. | |
| 2006/0154206 A1 | 7/2006 | Petersson et al. | |
| 2006/0167560 A1 | 7/2006 | Heck et al. | |
| 2006/0184187 A1 | 8/2006 | Surti | |
| 2006/0190002 A1 | 8/2006 | Tallarida | |
| 2006/0195112 A1 | 8/2006 | Ek | |
| 2006/0217728 A1 | 9/2006 | Chervitz et al. | |
| 2006/0229726 A1 | 10/2006 | Ek | |
| 2006/0271059 A1 | 11/2006 | Reay-Young et al. | |
| 2007/0005143 A1 | 1/2007 | Ek | |
| 2007/0038302 A1 | 2/2007 | Shultz et al. | |
| 2007/0038307 A1 | 2/2007 | Webster et al. | |
| 2007/0073394 A1 | 3/2007 | Seedhom et al. | |
| 2007/0093842 A1 | 4/2007 | Schmieding | |
| 2007/0093848 A1 | 4/2007 | Harris et al. | |
| 2007/0093890 A1 | 4/2007 | Eliasen et al. | |
| 2007/0093896 A1 | 4/2007 | Malinin | |
| 2007/0118136 A1 | 5/2007 | Ek | |
| 2007/0118224 A1 | 5/2007 | Shah et al. | |
| 2007/0123921 A1 | 5/2007 | Ek | |
| 2007/0134291 A1 | 6/2007 | Ting et al. | |
| 2007/0173850 A1 | 7/2007 | Rangaiah et al. | |
| 2007/0179608 A1 | 8/2007 | Ek | |
| 2007/0233128 A1 | 10/2007 | Schmieding et al. | |
| 2007/0244484 A1 | 10/2007 | Luginbuehl | |
| 2007/0250067 A1 | 10/2007 | Schmieding et al. | |
| 2007/0255399 A1 | 11/2007 | Eliasen et al. | |
| 2007/0255412 A1 | 11/2007 | Hajaj et al. | |
| 2007/0265700 A1 | 11/2007 | Eliasen et al. | |
| 2007/0270711 A1 | 11/2007 | Gil et al. | |
| 2007/0270873 A1 | 11/2007 | Flickinger et al. | |
| 2007/0282455 A1 | 12/2007 | Luginbuehl et al. | |
| 2007/0288031 A1 | 12/2007 | Dreyfuss et al. | |
| 2007/0299519 A1 | 12/2007 | Schmieding | |
| 2007/0299529 A1* | 12/2007 | Rhodes et al. | 623/20.32 |
| 2008/0004659 A1 | 1/2008 | Burkhart et al. | |
| 2008/0015607 A1 | 1/2008 | D'Alessio et al. | |
| 2008/0015709 A1 | 1/2008 | Evans et al. | |
| 2008/0027430 A1 | 1/2008 | Montgomery et al. | |
| 2008/0033443 A1 | 2/2008 | Sikora et al. | |
| 2008/0033447 A1 | 2/2008 | Sand | |
| 2008/0046084 A1 | 2/2008 | Sledge | |
| 2008/0071381 A1 | 3/2008 | Buscher et al. | |
| 2008/0086139 A1 | 4/2008 | Bourke et al. | |
| 2008/0086152 A1 | 4/2008 | McKay et al. | |
| 2008/0091271 A1 | 4/2008 | Bonitati et al. | |
| 2008/0091272 A1 | 4/2008 | Aram et al. | |
| 2008/0097618 A1 | 4/2008 | Baker et al. | |
| 2008/0103506 A1 | 5/2008 | Volpi et al. | |

(56) References Cited

U.S. PATENT DOCUMENTS

| | | |
|---|---|---|
| 2008/0114463 A1 | 5/2008 | Auger et al. |
| 2008/0138611 A1 | 6/2008 | Yasuzawa et al. |
| 2008/0154271 A1 | 6/2008 | Berberich et al. |
| 2008/0172125 A1 | 7/2008 | Ek |
| 2008/0177200 A1 | 7/2008 | Ikehara et al. |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0200904 A1 | 8/2008 | Cluff et al. |
| 2008/0208201 A1 | 8/2008 | Moindreau et al. |
| 2008/0243262 A1* | 10/2008 | Lee .................... 623/20.33 |
| 2008/0243263 A1* | 10/2008 | Lee et al. ............. 623/20.33 |
| 2008/0262500 A1 | 10/2008 | Collazo |
| 2008/0262625 A1 | 10/2008 | Spriano et al. |
| 2008/0275451 A1 | 11/2008 | McAllister et al. |
| 2008/0275512 A1 | 11/2008 | Albertirio et al. |
| 2008/0294168 A1 | 11/2008 | Wieland |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0018581 A1 | 1/2009 | Anderson et al. |
| 2009/0035722 A1 | 2/2009 | Balasundaram et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0088753 A1 | 4/2009 | Aram et al. |
| 2009/0088858 A1 | 4/2009 | Zinger et al. |
| 2009/0105772 A1* | 4/2009 | Seebeck et al. .......... 606/329 |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216268 A1 | 8/2009 | Panter |
| 2009/0216285 A1 | 8/2009 | Ek et al. |
| 2009/0220561 A1 | 9/2009 | Jin et al. |
| 2009/0222012 A1 | 9/2009 | Karnes et al. |
| 2009/0228031 A1 | 9/2009 | Ritter et al. |
| 2009/0228105 A1 | 9/2009 | Son et al. |
| 2009/0234452 A1 | 9/2009 | Steiner et al. |
| 2009/0254094 A1 | 10/2009 | Knapp et al. |
| 2009/0264889 A1 | 10/2009 | Long et al. |
| 2009/0264928 A1 | 10/2009 | Blain |
| 2009/0275950 A1 | 11/2009 | Sterrett et al. |
| 2009/0276052 A1 | 11/2009 | Regala et al. |
| 2009/0283701 A1 | 11/2009 | Ogawa |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0057197 A1 | 3/2010 | Weber et al. |
| 2010/0069958 A1 | 3/2010 | Sullivan et al. |
| 2010/0082035 A1 | 4/2010 | Keefer |
| 2010/0087829 A1 | 4/2010 | Metzger et al. |
| 2010/0092535 A1 | 4/2010 | Cook et al. |
| 2010/0112519 A1 | 5/2010 | Hall et al. |
| 2010/0136289 A1 | 6/2010 | Extrand et al. |
| 2010/0168505 A1 | 7/2010 | Inman et al. |
| 2010/0168854 A1 | 7/2010 | Luers et al. |
| 2010/0185294 A1 | 7/2010 | Ek |
| 2010/0191342 A1 | 7/2010 | Byrd et al. |
| 2010/0217315 A1 | 8/2010 | Jolly et al. |
| 2010/0227372 A1 | 9/2010 | Bilek et al. |
| 2010/0241236 A1 | 9/2010 | Katrana et al. |
| 2010/0249930 A1 | 9/2010 | Myers |
| 2010/0249935 A1 | 9/2010 | Slivka et al. |
| 2010/0249942 A1 | 9/2010 | Goswami et al. |
| 2010/0256645 A1 | 10/2010 | Zajac et al. |
| 2010/0256758 A1 | 10/2010 | Gordon et al. |
| 2010/0268227 A1 | 10/2010 | Tong et al. |
| 2010/0268238 A1 | 10/2010 | Sikora et al. |
| 2010/0268330 A1 | 10/2010 | Tong et al. |
| 2010/0268346 A1 | 10/2010 | Tong et al. |
| 2010/0268347 A1 | 10/2010 | Tong et al. |
| 2011/0009964 A1 | 1/2011 | Schwartz et al. |
| 2011/0035012 A1* | 2/2011 | Linares .................... 623/18.11 |
| 2011/0059312 A1 | 3/2011 | Howling et al. |
| 2011/0066242 A1 | 3/2011 | Lu et al. |
| 2011/0071641 A1 | 3/2011 | Ek et al. |
| 2011/0085968 A1 | 4/2011 | Jin et al. |
| 2011/0087280 A1 | 4/2011 | Albertorio |
| 2011/0093085 A1 | 4/2011 | Morton |
| 2011/0106271 A1 | 5/2011 | Regala et al. |
| 2011/0123951 A1 | 5/2011 | Lomicka |
| 2011/0125263 A1 | 5/2011 | Webster et al. |
| 2011/0125277 A1 | 5/2011 | Nygren et al. |
| 2011/0152869 A1 | 6/2011 | Ek et al. |
| 2011/0153023 A1 | 6/2011 | Deffenbaugh et al. |
| 2011/0159070 A1 | 6/2011 | Jin et al. |
| 2011/0190902 A1 | 8/2011 | Tong et al. |
| 2011/0196367 A1 | 8/2011 | Gallo |
| 2011/0213375 A1 | 9/2011 | Sikora et al. |
| 2011/0236435 A1 | 9/2011 | Biris |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0022656 A1 | 1/2012 | Lavi |
| 2012/0027837 A1 | 2/2012 | DeMuth et al. |
| 2012/0051489 A1 | 3/2012 | Varanasi et al. |
| 2012/0058328 A1 | 3/2012 | Tourvieille et al. |
| 2012/0059418 A1 | 3/2012 | Denham et al. |
| 2012/0065732 A1 | 3/2012 | Roller et al. |
| 2012/0065734 A1 | 3/2012 | Barrett et al. |
| 2012/0109136 A1 | 5/2012 | Bourque et al. |
| 2012/0109222 A1 | 5/2012 | Goel et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0128666 A1 | 5/2012 | Pébay et al. |
| 2012/0150225 A1 | 6/2012 | Burkart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0214128 A1 | 8/2012 | Collins et al. |
| 2012/0215310 A1 | 8/2012 | Sharp et al. |
| 2012/0221111 A1 | 8/2012 | Burkhead, Jr. et al. |
| 2012/0253467 A1 | 10/2012 | Frankle |
| 2012/0265298 A1 | 10/2012 | Schmieding et al. |
| 2012/0323338 A1 | 12/2012 | Vanasse |
| 2012/0330357 A1 | 12/2012 | Thal |
| 2013/0006374 A1 | 1/2013 | Le Couedic et al. |
| 2013/0022943 A1 | 1/2013 | Collins et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |
| 2013/0103104 A1 | 4/2013 | Krupp et al. |
| 2013/0110165 A1 | 5/2013 | Burkhart et al. |
| 2013/0138108 A1 | 5/2013 | Diyfuss et al. |
| 2013/0138150 A1 | 5/2013 | Baker et al. |
| 2013/0150885 A1 | 6/2013 | Dreyfuss |
| 2013/0150975 A1 | 6/2013 | Iannotti et al. |
| 2013/0165954 A1 | 6/2013 | Dreyfuss et al. |
| 2013/0165972 A1 | 6/2013 | Sullivan |
| 2013/0178871 A1 | 7/2013 | Koogle, Jr. et al. |
| 2013/0184818 A1 | 7/2013 | Coughlin et al. |
| 2013/0190819 A1 | 7/2013 | Norton |
| 2013/0190885 A1 | 7/2013 | Ammann et al. |
| 2013/0204257 A1 | 8/2013 | Zajac |
| 2013/0204259 A1 | 8/2013 | Zajac |
| 2013/0205936 A1 | 8/2013 | Schmieding et al. |
| 2013/0218176 A1 | 8/2013 | Denove et al. |
| 2013/0218286 A1 | 8/2013 | Stahl Wernersson et al. |
| 2013/0237987 A1 | 9/2013 | Graham |

(56) References Cited

U.S. PATENT DOCUMENTS

| | | |
|---|---|---|
| 2013/0238099 A1 | 9/2013 | Hardy et al. |
| 2013/0245775 A1 | 9/2013 | Metcalfe |
| 2013/0268073 A1 | 10/2013 | Albertorio et al. |
| 2013/0282129 A1 | 10/2013 | Phipps |
| 2013/0289570 A1 | 10/2013 | Chao |
| 2013/0304209 A1 | 11/2013 | Schmieding et al. |
| 2013/0331886 A1 | 12/2013 | Thornes |
| 2013/0338722 A1 | 12/2013 | Yalizis |
| 2013/0338792 A1 | 12/2013 | Schmieding et al. |
| 2013/0344600 A1 | 12/2013 | Jin et al. |
| 2013/0345747 A1 | 12/2013 | Dreyfuss |
| 2013/0345748 A1 | 12/2013 | Dreyfuss |
| 2014/0012267 A1 | 1/2014 | Skiora et al. |
| 2014/0012389 A1 | 1/2014 | Ek |
| 2014/0052178 A1 | 2/2014 | Dooney, Jr. |
| 2014/0052179 A1 | 2/2014 | Dreyfuss et al. |
| 2014/0066933 A1 | 3/2014 | Ek et al. |
| 2014/0074164 A1 | 3/2014 | Dreyfuss et al. |
| 2014/0074239 A1 | 3/2014 | Albertorio et al. |
| 2014/0079921 A1 | 3/2014 | De Voider |
| 2014/0081273 A1 | 3/2014 | Sherman |
| 2014/0081399 A1 | 3/2014 | Roller et al. |
| 2014/0088601 A1 | 3/2014 | Kuczynski |
| 2014/0088602 A1 | 3/2014 | Ammann et al. |
| 2014/0114322 A1 | 4/2014 | Perez, III |
| 2014/0114367 A1 | 4/2014 | Jolly et al. |
| 2014/0121700 A1 | 5/2014 | Dreyfuss et al. |
| 2014/0121701 A1 | 5/2014 | Dreyfuss et al. |
| 2014/0128889 A1 | 5/2014 | Sullivan et al. |
| 2014/0128915 A1 | 5/2014 | Dreyfuss et al. |
| 2014/0128921 A1 | 5/2014 | Parsons et al. |
| 2014/0155902 A1 | 6/2014 | Sikora et al. |
| 2014/0188232 A1 | 7/2014 | Metcalfe et al. |
| 2014/0194880 A1 | 7/2014 | Schmieding et al. |
| 2014/0228849 A1 | 8/2014 | Sterrett et al. |
| 2014/0236306 A1 | 8/2014 | Karnes et al. |
| 2014/0243439 A1 | 8/2014 | Papangelou et al. |
| 2014/0243891 A1 | 8/2014 | Schmieding et al. |
| 2014/0243892 A1 | 8/2014 | Choinski |
| 2014/0243976 A1 | 8/2014 | Schmieding et al. |
| 2014/0257297 A1 | 9/2014 | Koogle, Jr. et al. |
| 2014/0257299 A1 | 9/2014 | Berelsman et al. |
| 2014/0257384 A1 | 9/2014 | Dreyfuss et al. |
| 2014/0276841 A1 | 9/2014 | Albertorio et al. |
| 2014/0276990 A1 | 9/2014 | Perez, III |
| 2014/0277020 A1 | 9/2014 | Koogle et al. |
| 2014/0277121 A1 | 9/2014 | Pilgeram et al. |
| 2014/0277134 A1 | 9/2014 | ElAttrache et al. |
| 2014/0277181 A1 | 9/2014 | Garlock |
| 2014/0277186 A1 | 9/2014 | Granberry et al. |
| 2014/0277214 A1 | 9/2014 | Helenbolt et al. |
| 2014/0277448 A1 | 9/2014 | Guerra et al. |
| 2014/0288657 A1 | 9/2014 | Lederman et al. |
| 2014/0309689 A1 | 10/2014 | Sikora et al. |
| 2014/0324167 A1 | 10/2014 | Schmieding et al. |
| 2014/0335145 A1 | 11/2014 | Jin et al. |
| 2014/0350688 A1 | 11/2014 | Michel et al. |
| 2015/0073424 A1 | 3/2015 | Couture et al. |
| 2015/0134066 A1 | 5/2015 | Bachmaier |
| 2015/0142052 A1 | 5/2015 | Koogle, Jr. et al. |
| 2015/0157462 A1 | 6/2015 | Ek et al. |
| 2015/0164648 A1 | 6/2015 | Lizak et al. |
| 2015/0201951 A1 | 7/2015 | Bradley et al. |
| 2015/0216541 A1 | 8/2015 | Schmieding et al. |
| 2015/0245831 A1 | 9/2015 | Sullivan |
| 2015/0250472 A1 | 9/2015 | Ek et al. |
| 2015/0250475 A1 | 9/2015 | Ek |
| 2015/0250594 A1 | 9/2015 | Ek |
| 2015/0250602 A1 | 9/2015 | Sikora et al. |
| 2015/0265328 A1 | 9/2015 | Viola |
| 2015/0313586 A1 | 11/2015 | Burkhart et al. |
| 2016/0022374 A1 | 1/2016 | Haider |
| 2016/0030035 A1 | 2/2016 | Zajac et al. |
| 2016/0051268 A1 | 2/2016 | Seitlinger et al. |
| 2016/0106444 A1 | 4/2016 | Ek |
| 2016/0151060 A1 | 6/2016 | Albertorio et al. |
| 2016/0151119 A1 | 6/2016 | Michel et al. |
| 2016/0287243 A1 | 10/2016 | Benedict et al. |
| 2016/0287266 A1 | 10/2016 | Sikora et al. |
| 2016/0310132 A1 | 10/2016 | Meislin et al. |
| 2016/0331404 A1 | 11/2016 | Jolly et al. |
| 2016/0354197 A1 | 12/2016 | Roller et al. |
| 2017/0056180 A1 | 3/2017 | Schmieding |
| 2017/0100251 A1 | 4/2017 | Ek et al. |
| 2017/0119528 A1 | 5/2017 | Ek et al. |
| 2017/0128085 A1 | 5/2017 | Sikora et al. |
| 2017/0209196 A1 | 7/2017 | Zajac et al. |
| 2017/0215935 A1 | 8/2017 | Taft |
| 2017/0239696 A1 | 8/2017 | Weber |
| 2017/0252147 A1 | 9/2017 | Albertorio et al. |
| 2017/0252521 A1 | 9/2017 | Guerra et al. |
| 2017/0281200 A1 | 10/2017 | Sikora et al. |
| 2017/0296328 A1 | 10/2017 | Albertorio et al. |
| 2017/0311983 A1 | 11/2017 | Sikora et al. |
| 2017/0333020 A1 | 11/2017 | Laviano et al. |
| 2018/0055507 A1 | 3/2018 | Bachmaier et al. |
| 2018/0085104 A1 | 3/2018 | Schmieding et al. |
| 2018/0085109 A1 | 3/2018 | Petry et al. |
| 2018/0103963 A1 | 4/2018 | Bradley et al. |
| 2018/0116682 A1 | 5/2018 | Albertorio et al. |
| 2018/0132869 A1 | 5/2018 | Sikora et al. |
| 2018/0154041 A1 | 6/2018 | Altschuler et al. |
| 2018/0344447 A1 | 12/2018 | Albertorio et al. |
| 2019/0021719 A1 | 1/2019 | Dooney et al. |
| 2019/0029836 A1 | 1/2019 | Ek |
| 2019/0038426 A1 | 2/2019 | Ek |
| 2019/0059910 A1 | 2/2019 | Adams et al. |
| 2019/0105160 A1 | 4/2019 | Ek et al. |
| 2019/0105165 A1 | 4/2019 | Sikora et al. |
| 2019/0105166 A1 | 4/2019 | Ek et al. |
| 2019/0201185 A1 | 7/2019 | Albertorio et al. |
| 2019/0239902 A1 | 8/2019 | Sikora et al. |
| 2019/0350578 A1 | 11/2019 | Petry et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| DE | 19505083 | 11/1995 |
| DE | 102004053606 | 5/2006 |
| DE | 112013003358 | 3/2015 |
| EP | 0240004 | 10/1987 |
| EP | 0241240 | 10/1987 |
| EP | 0290736 | 11/1988 |
| EP | 0350780 | 1/1990 |
| EP | 0485678 | 5/1992 |
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0993812 | 4/2000 |
| EP | 0661023 | 8/2001 |
| EP | 1374782 | 1/2004 |
| EP | 1426013 | 9/2004 |
| EP | 1870060 | 12/2007 |
| EP | 1927328 | 6/2008 |
| EP | 1278460 | 4/2009 |
| EP | 2062541 | 5/2009 |
| EP | 2455002 | 5/2012 |
| EP | 2314257 | 2/2013 |
| EP | 2572650 | 3/2013 |
| EP | 2804565 | 10/2014 |
| EP | 2481368 | 12/2014 |

(56) References Cited

FOREIGN PATENT DOCUMENTS

| | | |
|---|---|---|
| EP | 2986232 | 2/2016 |
| EP | 2 400 930 | 12/2017 |
| EP | 2986232 | 11/2018 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2964035 | 10/1999 |
| JP | 2001525210 | 12/2001 |
| JP | 2002291779 | 10/2002 |
| JP | 2003534096 | 11/2003 |
| WO | 198803781 | 6/1988 |
| WO | 8909578 | 10/1989 |
| WO | 9409730 | 5/1994 |
| WO | 9427507 | 12/1994 |
| WO | 9624304 | 8/1996 |
| WO | 1997022306 | 6/1997 |
| WO | 199725006 | 7/1997 |
| WO | 9920192 | 4/1999 |
| WO | 0013597 | 3/2000 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2004100839 | 11/2004 |
| WO | 2005051231 | 6/2005 |
| WO | 2006004885 | 1/2006 |
| WO | 2006074321 | 7/2006 |
| WO | 2006091686 | 8/2006 |
| WO | 2010135156 | 11/2010 |
| WO | 2012003548 | 1/2012 |
| WO | 2012021857 | 2/2012 |
| WO | 2012058349 | 5/2012 |
| WO | 2013152102 | 10/2013 |
| WO | 2014008126 | 1/2014 |
| WO | 2014172347 | 10/2014 |
| WO | 2016154393 | 9/2016 |
| WO | 2019028344 | 2/2019 |

OTHER PUBLICATIONS

Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).

Thermann, et al, ATOS Newsletter, 06/05, Aktuelle Therrien, (16 pages).

Henry, Henry, Anatomy of the Human Body, 1918, 6d. The Foot 1.

The Tarsus, II. Osteology, cover page and 10 pgs, www.Bartleby.com/107/63.html#i268 Oct. 25, 2004.

Chainsaw, Wikipedia, the free encyclopedia, http://en.wikipedia.org/w/index.php?title=Chainsaw&printable=yes, Jun. 26, 2007 (3 pages).

Apta | Knee,/http://www.apta.org/AM/PrinerTemplate.cfm?Section=Home&Template=/CM/HTMLDisplay.dfg& . . . Jun. 25, 2007 (1page).

American Machinist, Full-radius milling cutters, http://www.americanmachinist.com/Classes/Article/ArticleDraw_P.aspx, Jun. 26, 2007 (1 page).

Chuck (engineering),Wikipedia, the free encyclopedia, http://en.wikipedia.org/w/index.php?title=Chuck_%28engineering%29&printable=yes, Jun. 25, 2007, (4 pages).

Dovetail Rails, http://www.siskiyou.com/MDRSeries.htm, Jun. 25, 2007 (2 pages).

Knee Resurfacing, Permedica, GKS, Global Knee System. Cod. 104570 vers 1.0 del Mar. 15, 2006 (8pages).

Makita Industrial Power Tools, Product Details Print Out, Chain Mortiser, http://www.makita.com/menu.php?pg=product_det_prn&tag=7104L, Jun. 26, 2007 (3pgs).

Milling machine, Wikipedia, the free encyclopedia, http://en.wikipedia.org/w/index.php?title=Milling_machine&printable=yes, Jun. 26, 2007 (4 pages).

Mortise and tenon, Wikipedia, the free encyclopedia, http://en.wikipedia.org/w/index.php?title=Mortise_and_tenon&printable=yes, Jun. 25, 2007 (3 pages).

Oka et al, "Development of artificial articular cartilage", Proc Instn Mech Engrs vol. 214 Part H, 2000 pp. 59-68 (10 pages).

M. Siguier, MD et al, "Preliminary Results of Partial Surface Replacement of the Femoral Head in Osteonecrosis", The Journal of Arthroplasty, vol. 14, No. 1, 1999, pp. 45-51.

T. Siguier, MD et al, Partial Resurfacing Arthroplasty of the Femoral Head in Avascular Necrosis, Clinical Orthopaedics and Related Research, No. 386, 2001, pp. 85-92.

Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).

The Mini Uni: A New Solution for Arthritic Knee Pain and Disability, AORI, 4 pages, www.aori.org/uniknee.htm Apr. 20, 2004.

The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.

Ushio et al, "Partial hemiarthroplasty for the treatment of osteonecrosis of the femoral head", An Experimental Study in the Dog, The Journal of Bone and Joint Surgery, vol. 85-B, No. 6, Aug. 2003, pp. 922-930 (9 pages).

Russell E. Windsor, MD, In-Depth Topic Reviews, Unicompartmental Knee Replacement, Nov. 7, 2002, 9 pages.

Yaw angle, Wikipedia, the free encyclopedia, http://en.wikipedia.org/w/index.php?title=Yaw_angle&printable=yes, Jun. 25, 2007 (1 page).

Bale, MD, Reto J., et al, "Osteochondral Lesions of the Talus: Computer=assisted Retrograde Drilling Feasibility and Accuracy in Initial Experiences[1]", (Radiology. 2001;218:278-282)© RSNA, 2001.

Biomet/Copeland, "Aequalis® Resurfacing Head" Tornier, Scientific Vision, Surgical Leadership, SS-401 Jan. 2007.

Kumai, M.D., Tsukasa, et al Arthroscopic Drilling for the Treatment of Osteochondral Lesions of the Talus*, The Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 Jul.-Aug. 2001:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

(56) References Cited

OTHER PUBLICATIONS

Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, A service of the National Library of Medicine and the National Institutes of Health, Foot Ankle Int.Aug. 1999; 20 (8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.
USPTO Office Action dated Dec. 21, 2007 issued in corresponding U.S. Appl. No. 11/693,26.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No, 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12027121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Feb. 14, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Ascension Orthopedics, Inc., Ascension Orthopedics Announces Market Release of Titan™ Inset Mini Glenoid, PR Newswire, downloaded from internet Jul. 18, 2011, http://www.orthospinenews.

(56) References Cited

OTHER PUBLICATIONS com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
European Office Action dated Apr. 16, 2013 issued in European Patent Application No. 12 002 103.5, 5 pages.
U.S. Applicant Initiated Interview Summary dated May 15, 2013 issued in U.S. Appl. No. 12/762,920, 3 pages.
European Office Action dated May 15, 2013 issued in European Patent Application No. 05 763 817.3, 4 pages.
U.S. Final Office Action dated Jun. 5, 2013 issued in U.S. Appl. No. 12/942,923, 26 pages.
U.S. Final Office Action dated Jun. 24, 2013 issued in U.S. Appl. No. 13/042,382, 28 pages.
U.S. Notice of Allowance dated Jun. 14, 2013 issued in U.S. Appl. No. 13/043,430, 10 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.
Corrected Notice of Allowability dated Sep. 10, 2013 issued in U.S. Appl. No. 13/043,430, 7 pages.
Decision to Grant dated Sep. 19, 2013 issued in European Patent Application No. 07862736.1, 1 page.
U.S. Office Action dated Oct. 8, 2013 issued in U.S. Appl. No. 13/438,095, 8 pages.
International Search Report and Written Opinion dated Oct. 22, 2013 issued in PCT International Patent Application No. PCT/US2013/048569, 15 pages.
Notice of Allowance dated Oct. 30, 2013 issued in U.S. Appl. No. 13/037,998, 28 pages.
U.S. Final Office Action dated Nov. 29, 2013 issued in U.S. Appl. No. 12/762,920, 9 pages.
U.S. Final Office Action dated Dec. 5, 2013 issued in U.S. Appl. No. 13/470,678, 8 pages.
U.S. Office Action dated Dec. 12, 2013 issued in U.S. Appl. No. 12/979,992, 12 pages.
U.S. Office Action dated Dec. 17, 2013 issued in U.S. Appl. No. 12/001,473, 21 pages.
U.S. Office Action dated Feb. 5, 2014, issued in U.S. Appl. No. 13/438,095, 9 pages.
U.S. Office Action dated Feb. 7, 2014, issued in U.S. Appl. No. 13/075,006, 9 pages.
Australian Examination Report dated Feb. 7, 2014, issued in Australian Patent Application No. 2010236182, 3 pages.
Australian Examination Report dated Feb. 14, 2014, issued in Australian Patent Application No. 2011222404, 3 pages.
European Extended Search Report dated Feb. 24, 2014, issue in European Patent Application No. 09716273.9, 7 pages.
Australian Examination Report dated Feb. 28, 2014, issued in Australian Patent Application No. 2010217907, 3 pages.
U.S. Final Office Action dated Mar. 20, 2014, issued in U.S. Appl. No. 12/711,039, 17 pages.
European Examination Report dated Mar. 20, 2014, issued in European Patent Application No. 12 002 103.5, 3 pages.
U.S. Office Action dated Mar. 21, 2014, issued in U.S. Appl. No. 12/942,923, 6 pages.
U.S. Notice of Allowance dated Apr. 1, 2014, issued in U.S. Appl. No. 13/470,678, 7 pages.
Australian Examination Report dated Apr. 3, 2014, issued in Australian Patent Application No. 2010217907, 3 pages.
U.S. Office Action dated Apr. 29, 2014, issued in U.S. Appl. No. 13/037,929, 11 pages.
U.S. Office Action dated May 19, 2014, issued in U.S. Appl. No. 13/436,188, 10 pages.
U.S. Office Action dated May 28 2014, issued in U.S. Appl. No. 13/752,858, 8 pages.
U.S. Office Action dated Jun. 4, 2014, issued in U.S. Appl. No. 12/762,920, 10 pages.
Notice of Allowance dated Jun. 19, 2014, issued in U.S. Appl. No. 13/470,678, 5 pages.
Intent to Grant dated Jun. 27, 2014, issued in European Patent Application No. 12 002 103.5, 6 pages.
U.S. Office Action dated Jul. 7, 2014, issued in U.S. Appl. No. 12/979,992, 6 pages.
U.S. Office Action dated Jul. 7, 2014, issued in U.S. Appl. No. 12/001,473, 15 pages.
U.S. Office Action dated Aug. 13, 2014, issued in U.S. Appl. No. 12/762,948, 12 pages.
U.S. Notice of Allowance dated Aug. 21, 2014, issued in U.S. Appl. No. 13/075,006, 5 pages.
U.S. Office Action dated Sep. 18, 2014, issued in U.S. Appl. No. 13/785,867, 8 pages.
U.S. Notice of Allowance dated Oct. 6, 2014, issued in U.S. Appl. No. 12/942,923, 5 pages.
U.S. Office Action issued in U.S. Appl. No. 13/438,095, dated Nov. 4, 2014, 11 pages.
International Search Report and Written Opinion issued in PCT Patent Application Serial No. PCT/US14/34157, dated Nov. 4, 2014, 12 pages.
European Extended Search Report issued in European Patent Application Serial No. 10765332.1, dated Nov. 10, 2014, 6 pages.
U.S. Office Action issued in U.S. Appl. No. 12/711,039, dated Nov. 10, 2014, 10 pages.
European Extended Search Report issued in European Patent Application Serial No. 10746863.9, dated Nov. 13, 2014, 5 pages.
European Decision to Grant issued in European Patent Application Serial No. 12002103.5, dated Nov. 20, 2014, 1 page.
European Office Action issued in European Patent Application No. 08 729 178.7, dated Nov. 25, 2014, 4 pages.
U.S. Notice of Allowance issued in U.S. Appl. No. 13/037,929, dated Dec. 11, 2014, 5 pages.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance dated Sep. 26, 2003 in U.S. Appl. No. 10/162,533.
USPTO Notice of Allowance dated May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance dated Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patent application No. 2005202099.
AU Examiners report dated Jan. 12, 2007 issued in corresponding Australian patent application No. 2006202337.
AU Examiners report dated Feb. 21, 2007 issued in corresponding Australian patent application No. 2005202099.
AU Examiners report dated May 23, 2007 issued in corresponding Australian patent application No. 2005202099.

(56) References Cited

OTHER PUBLICATIONS

AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
U.S. Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.

(56) References Cited

OTHER PUBLICATIONS

Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Notice of Allowability dated Oct. 9, 2012, issued in U.S. Appl. No. 12/713,135, 5 pages.
Notice of Allowability dated Oct. 11, 2012, issued in U.S. Appl. No. 11/169,326 2 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31 2012, issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.
Extended European Search report dated Dec. 10, 2012 issued in European Patent Application No. 07844549.1, 6 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
U.S. Office Action dated Feb. 25, 2013 issued in U.S. Appl. No. 12/762,920, 8 pages.
Canadian Office Action dated Dec. 13, 2012 issued in Canadian Patent Application No. 2,407,440, 6 pages.
International Search Report and Written Opinion dated Mar. 8, 2013 issued in PCT Patent Application No. PCT/US12/71199, 13 pages.
U.S. Office Action dated Apr. 15, 2013 issued in U.S. Appl. No. 13/470,678, 10 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. 12/762,948, 10 pages.
Sullivan, "Hallux Rigidus: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Becher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
U.S. Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 28, 2009 issued in related U.S. Appl. No. 11/359,891.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Reasons for Rejection issued in related Japanese Patent Application No. 2003-394702 dated Jul. 21, 2009.
Notice of Reasons for Rejection issued in related Japanese Patent Application No. 20-541615 dated May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.

(56) References Cited

OTHER PUBLICATIONS

Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
International Preliminary Report on Patentability dated Jan. 15, 2015, issued in PCT Patent Application No. PCT/US2013/048569.
Notice of Allowance dated Jan. 21, 2015, issued in U.S. Appl. No. 13/752,858, 7 pages.
Notice of Allowability dated Feb. 19, 2015, issued in U.S. Appl. No. 13/037,929, 2 pages.
U.S. Office Action dated Feb. 19, 2015, issued in U.S. Appl. No. 14/035,061, 6 pages.
Notice of Allowance dated Feb. 25, 2015, issued in U.S. Appl. No. 13/436,188, 8 pages.
Office Action dated Mar. 3, 2015, issued in U.S. Appl. No. 12/979,992, 11 pages.
Canadian Office Action dated Feb. 27, 2015 issued in Canadian Patent Application Serial No. 2,407,440, 7 pages.
International Search Report and Written Opinion dated Aug. 8, 2007 issued in corresponding PCT patent application No. PCT/US06/29875.
Notice of Allowance issued in corresponding U.S. Application No. 10308718 dated Sep. 11, 2006.
Office Action issued in corresponding U.S. Application No. 11326133 dated Oct. 17, 2007.
United States Office Action issued is related U.S. Patent Application No. 10760965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action issued in related U.S. Patent Application No. 11326133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Patent Application No. 10994453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
McCarty, III., et al., "Nonarthroplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al, "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.

(56) References Cited

OTHER PUBLICATIONS

Jäger, et al., "Partial hemi-resurfacing of the hip joint—a new approach to treat local osteochondral defects?" Biomed Tech 2006; 51:371-376 (2006).
Intent to Grant dated Jul. 8, 2015, issued in European Patent Application No. 08 729 178.7, 7 pages.
Extended Search Report dated Sep. 9, 2015, issued in European Patent Application No. 11751521.3, 13 pages.
European Examination Report dated Jul. 22, 2015, issued in European Patent Application No. 09 002 088.4, 4 pages.
International Preliminary Report on Patentability dated Oct. 29, 2015, issued in PCT Patent Application No. PCT/US/2014/034157, 5 pages.
European Examination Report dated Oct. 28, 2015, issued in European Patent Application No. 05 763 817.3, 4 pages.
U.S. Notice of Allowance dated Oct. 30, 2015, issued in U.S. Appl. No. 12/762,920, 8 pages.
Partial Supplementary European Search Report dated Nov. 5, 2015, issued in European Patent Application No. 2860168.9, 6 pages.
U.S. Office Action dated Nov. 17, 2015, issued in U.S. Appl. No. 13/930,737, 9 pages.
U.S. Office Action dated Nov. 25, 2015, issued in U.S. Appl. No. 13/723,902, 13 pages.
U.S. Office Action dated Nov. 25, 2015, issued in U.S. Appl. No. 13/863,917, 12 pages.
European Examination Report dated Dec. 7, 2015, issued in European Patent Application No. 10 765 332.1, 4 pages.
U.S. Office Action dated Dec. 8, 2015, issued in U.S. Appl. No. 13/796,675, 16 pages.
European Decision to Grant dated Dec. 17, 2015, issued in European Patent Application No. 08729178.7, 2 pages.
Partial supplementary European search report dated Mar. 25, 2015, issued in EP Patent Application No. 11751521.3, 6 pages.
U.S. Final Office Action dated Jun. 2, 2015, issued in U.S. Appl. No. 12/001,473, 18 pages.
U.S. Examiner interview summary dated Apr. 8, 2015, issued in U.S. Appl. No. 12/001,473, 4 pages.
U.S. Final Office Action dated Apr. 16, 2015, issued in U.S. Appl. No. 12/762,920, 15 pages.
U.S. Supplemental Notice of Allowance dated Apr. 21, 2015, issued in U.S. Appl. No. 13/436,188, 6 pages.
U.S. Final Office Action dated Apr. 28, 2015, issued in U.S. Appl. No. 13/785,867, 8 pages.
U.S. Final Office Action dated May 22, 2015, issued in U.S. Appl. No. 13/438,095, 7 pages.
U.S. Office Action dated Jun. 25, 2015, issued in U.S. Appl. No. 12/711,039, 10 pages.
U.S. Final Office Action dated Jul. 7, 2015, issued in U.S. Appl. No. 12/762,948, 15 pages.
Notice of Allowance dated Jul. 31, 2015, issued in U.S. Appl. No. 13/438,095, 8 pages.
U.S. Final Office Action dated Sep. 17, 2015, issued in U.S. Appl. No. 14/035,061, 10 pages.
U.S. Office Action dated Jan. 21, 2016, issued in U.S. Appl. No. 12/762,948, 14 pages.
U.S. Office Action dated Mar. 22, 2016, issued in U.S. Appl. No. 14/640,602, 8 pages.
U.S. Notice of Allowance dated Feb. 8, 2016, issued in U.S. Appl. No. 13/785,867, 8 pages.
U.S. Notice of Allowance dated Feb. 12, 2016, issued in U.S. Appl. No. 12/001,473, 14 pages.
Canadian Office Action dated Feb. 15, 2016, issued in Canadian Patent Application No. 2,407,440, 3 pages.
U.S. Notice of Allowability dated Feb. 17, 2016, issued in U.S. Appl. No. 13/785,867, 4 pages.
U.S. Notice of Allowance dated Feb. 17, 2016, issued in U.S. Appl. No. 12/979,992, 5 pages.
U.S. Final Office Action dated Feb. 25, 2016, issued in U.S. Appl. No. 12/711,039, 7 pages.
European Extended Search Report dated Feb. 29, 2016, issued in European Patent Application No. 12860168.9, 11 pages.
Canadian Examiner Requisition dated Mar. 10, 2016, issued in Canadian Patent Application No. 2,759,027, 3 pages.
European Examination Report dated Mar. 21, 2016, issued in European Patent Application No. 10 746 863.9, 3 pages.
U.S. Office Action dated Jun. 2, 2016, issued in U.S. Appl. No. 14/035,061, 9 pages.
U.S. Notice of Allowance dated Jun. 7, 2016, issued in U.S. Appl. No. 13/930,737, 5 pages.
International Search Report and Written Opinion dated, Jun. 10, 2016, issued in PCT Patent Application No. PCT/US2016/023930, 13 pages.
U.S. Notice of Allowance dated Jun. 29, 2016, issued in U.S. Appl. No. 13/863,917, 9 pages.
U.S. Final Office Action dated Jul. 6, 2016, issued in U.S. Appl. No. 13/723,902, 15 pages.
Official Communication dated Jun. 21, 2016, issued in European Patent Application No. 11 751 521.3, 3 pages.
Official Communication dated Aug. 23, 2016, issued in European Patent Application No. 10 765 332.1, 4 pages.
Office Action dated Nov. 22, 2016, issued in U.S. Appl. No. 14/640,774, 10 pages.
Final Office Action dated Sep. 30, 2016, issued in U.S. Appl. No. 14/640,602, 5 pages.
Extended Search Report dated Nov. 16, 2016, issued in European Patent Application No. 14785702.3, 7 pages.
Office Action dated Nov. 24, 2016, issued in European Patent Application No. 12 860 168.9, 4 pages.
Office Action dated Oct. 10, 2016, issued in European Patent Application No. 10 746 863.9, 4 pages.
Office Action dated Dec. 1, 2016, issued in European Patent Application No. 05 763 817.3, 3 pages.
Final Office Action dated Jul. 19, 2016, issued in U.S. Appl. No. 13/796,675, 17 pages.
Office Action dated Sep. 8, 2016, issued in U.S. Appl. No. 14/640,529, 15 pages.
Canadian Office Action dated Jan. 9, 2017, issued in Canadian Patent Application No. 2,759,027, 3 pages.
Canadian Office Action dated Mar. 22, 2017, issued in Canadian Patent Application No. 2,407,440, 7 pages.
U.S. Notice of Allowance dated Apr. 14, 2017, issued in U.S. Appl. No. 14/640,602, 7 pages.
U.S. Office Action dated Apr. 28, 2017, issued in U.S. Appl. No. 15/153,113, 11 pages.
U.S. Final Office Action dated May 9, 2017, issued in U.S. Appl. No. 14/640,529, 15 pages.
U.S. Final Office Action dated Jun. 15, 2017, issued in U.S. Appl. No. 14/640,774, 10 pages.
Notice of Allowance dated Aug. 7, 2017, issued in U.S. Appl. No. 14/640,602, 8 pages.
Office Action dated Aug. 25, 2017, issued in U.S. Appl. No. 14/728,216, 10 pages.
Final Office Action dated Aug. 25, 2017, issued in U.S. Appl. No. 14/035,061, 10 pages.
Final Office Action dated Sep. 22, 2017, issued in U.S. Appl. No. 13/723,902, 21 pages.
Preliminary Report on Patentability dated Oct. 5, 2017, issued in PCT Patent Application No. PCT/US2016/023930, 11 pages.
Intent to Grant dated Oct. 6, 2017, issued in European Patent Application No. 11 751 521.3, 7 pages.
Final Office Action dated Oct. 6, 2017, issued in U.S. Appl. No. 13/796,675, 18 pages.
Intent to Grant dated Oct. 6, 2017, issued in European Patent Application No. 12 860 168.9, 7 pages.
Office Action dated Oct. 16, 2017, issued in European Patent Application No. 05 763 817.3, 5 pages.
Office Action dated Oct. 17, 2017, issued in U.S. Appl. No. 14/640,667, 10 pages.
Office Action dated Oct. 16, 2017, issued in Canadian Patent Application No. 2,759,027, 3 pages.
Notice of Allowance dated Jan. 27, 2017, issued in U.S. Appl. No. 12/762,948, 5 pages.

(56) References Cited

OTHER PUBLICATIONS

Office Action dated Jan. 27, 2017, issued in U.S. Appl. No. 14/035,061, 9 pages.
Office Action dated Feb. 7, 2017, issued in U.S. Appl. No. 13/723,902, 16 pages.
Office Action dated Feb. 22, 2017, issued in U.S. Appl. No. 13/796,675, 19 pages.
European Intent to Grant dated Dec. 1, 2017, issued in European Patent Application Serial No. 09 002 088.4, 6 pages.
Canadian Notice of Allowance dated Dec. 14, 2017, issued in Canadian Patent Application Serial No. 2,407,440, 1 page.
U.S. Notice of Allowance dated Apr. 16, 2018, issued in U.S. Appl. No. 15/153,170, 10 pages.
Office Action dated May 16, 2018, issued in U.S. Appl. No. 15/388,808, 7 pages.
U.S. Notice of Allowance dated May 16, 2018, issued in U.S. Appl. No. 14/728,216, 5 pages.
Office Action dated May 31, 2018, issued in U.S. Appl. No. 13/732,902, 15 pages.
Office Action dated Jun. 19, 2018, issued in U.S. Appl. No. 15/296,772, 8 pages.
Office Action dated Jun. 29, 2018, issued in U.S. Appl. No. 14/640,667, 11 pages.
U.S. Notice of Allowance dated Nov. 30, 2017, issued in U.S. Appl. No. 14/640,529, 7 pages.
U.S. Notice of Allowance dated Jan. 10, 2018, issued in U.S. Appl. No. 141640,774, 8 pages.
U.S. Notice of Allowance dated Dec. 8, 2017, issued in U.S. Appl. No. 15/153,113, 5 pages.
Notice of Allowance dated Jan. 22, 2019, issued in U.S. Appl. No. 15/296,772, 7 pages.
Office Action dated Dec. 21, 2018, issued in U.S. Appl. No. 15/388,808, 7 pages.
Extended Search Report dated Nov. 26, 2018, issued in European Patent Application No. 16769660.8, 7 pages.
Office Action dated Sep. 5, 2018, issued in U.S. Appl. No. 15/606,643, 6 pages.
Office Action dated Nov. 9, 2018, issued in Canadian Patent Application No. 2,759,027, 4 pages.
International Search Report and Written Opinion dated Oct. 23, 2018, issued in PCT Patent Application No. PCT/US18145157, 11 pages.
Office Action dated Sep. 11, 2019, issued in U.S. Appl. No. 15/351,530, 15 pages.
Notice of Allowance dated Jun. 11, 2019, issued in Canadian Patent Application No. 2,759,027, 1 page.
Examination Report dated Jul. 2, 2019, issued in Brazilian Patent Application No. PI1014961-9, 2 pages.
Notice of Allowance dated Jul. 15, 2019, issued in U.S. Appl. No. 15/606,643, 5 pages.
Notice of Allowance dated Sep. 10, 2019, issued in U.S. Appl. No. 15/388,808, 8 pages.
Office Action dated Mar. 1, 2019, issued in U.S. Appl. No. 15/388,808, 9 pages.
Office Action dated Apr. 2, 2019, issued in U.S. Appl. No. 13/723,902, 19 pages.
Office Action dated Apr. 10, 2019, issued in U.S. Appl. No. 15/865,734, 8 pages.
Office Action dated May 9, 2019, issued in U.S. Appl. No. 15/943,949, 8 pages.
Office Action dated May 15, 2019, issued in U.S. Appl. No. 14/640,667, 16 pages.
Office Action dated May 15, 2019, issued in U.S. Appl. No. 15/973,981, 6 pages.
Notice of allowance dated Oct. 28, 2019, issued in U.S. Appl. No. 15/865,734, 7 pages.
Office Action dated Nov. 19, 2019, issued in U.S. Appl. No. 13/723,902, 16 pages.
Notice of allowance dated Dec. 12, 2019, issued in U.S. Appl. No. 15/388,808, 8 pages.
Notice of allowance dated Dec. 16, 2019, issued in U.S. Appl. No. 15/973,981, 8 pages.
Notice of allowance dated Dec. 17, 2019, issued in U.S. Appl. No. 15/943,949, 7 pages.
Office Action dated Jan. 16, 2020, issued in U.S. Appl. No. 14/640,667, 10 pages.
Office Action dated Dec. 30, 3019, issued in U.S. Appl. No. 15/943,956, 16 pages.
International Search Report and Written Opinion dated Jan. 16, 2020, issued in PCT International Patent Application No. PCT/US2019/058517, 9 pages.

* cited by examiner

TIBIAL RESURFACING SYSTEM AND METHOD

CROSS REFERENCE TO RELATED APPLICATIONS

This application is a division of U.S. patent application Ser. No. 13/042,382, filed Mar. 7, 2011, which claims the benefit of U.S. Provisional Patent Application No. 61/310,774, filed Mar. 5, 2010, which is fully incorporated herein by reference. This application is also a continuation-in-part of U.S. patent application Ser. No. 11/779,044, filed Jul. 17, 2007, which claims the benefit of U.S. Provisional Patent Application Ser. No. 60/807,538, filed Jul. 17, 2006, the entire disclosures of all of which are incorporated fully herein by reference.

FIELD

This disclosure relates to devices and methods for the repair of defects that occur in articular cartilage on the surface of bones, particularly the knee.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF THE DRAWINGS

Features and advantages of the present invention are set forth by description of embodiments consistent with the present invention, which description should be considered in conjunction with the accompanying drawings wherein.

DETAILED DESCRIPTION

By way of summary, one embodiment of the present disclosure may feature a system and method for repairing a portion of the articular surface proximate to a defect. While the present disclosure will be described in terms of a system and method for repairing a portion of the tibial articular surface, it should be understood that the system and method may be used to repair other articular surfaces (such as, but not limited to, femoral articular surfaces and the like). The system and method may include securing a one or more guides/jigs defining one or more passageways to a portion of the tibia (e.g., immediately below the tibial articular surface) proximate to the defect. The passageways may define a generally cylindrical core pathway for a drill bit (i.e., a coring drill bit). When the guide is secured to the femur, the generally cylindrical core pathway may partially intersect/overlap with the articular surface and a portion of the bone beneath the articular surface. A first truncated cylindrical excision site may be formed in the articular surface and/or bone beneath the articular surface by advancing the drill along the core pathway. The drill may have a diameter large enough to remove a portion of the articular surface as it is advanced through the guide and into the articular surface. Additional truncated cylindrical excision sites may also be formed. One or more of the additional truncated cylindrical excision sites may partially overlap with adjacent truncated cylindrical excision sites.

The guide and/or the drill may include a depth feature configured to control the depth of the truncated cylindrical excision site formed in the articular surface/bone. The depth feature may prevent the drill from being advanced too far, thereby preventing the drill from accidentally damaging any structures proximate to the excision sites (e.g., nerves). The system and method may also include an implant having a load bearing surface having a surface contour/geometry based on the surface contour/geometry of the patient's original removed articular surface. For example, the surface contour/geometry of the load bearing surface may be based on one or more measurements taken of the patient's original articular surface. The implant may also feature a bone facing or distal surface having a surface contour/geometry configured to be received in the truncated cylindrical excision sites.

Figure 1:
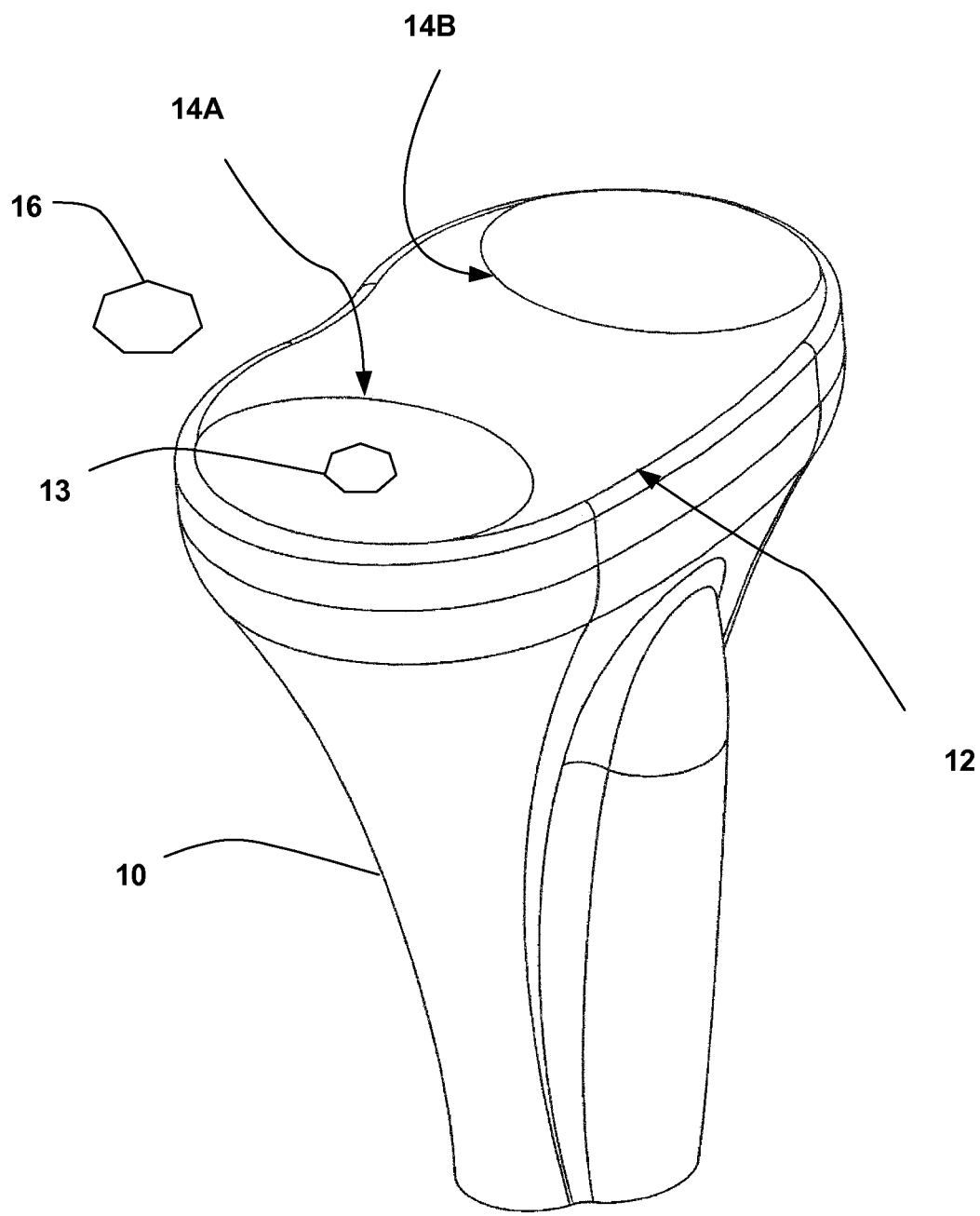
FIG. 1 is a schematic diagram illustrating an incision proximate the knee.

Turning now to FIG. 1, a tibia 10 is generally illustrated. As may be appreciated, the tibial articular surface 12 may include a tibial plateau comprising a plurality of concaved surfaces 14a, 14b configured to articulate with the femoral condyles (not shown for clarity). It may be further appreciated that the tibial articular surface 12 may include additional concaved surfaces not shown for the sake of clarity. One or more of the concaved surfaces (e.g., concaved surface 14a) may include a defect 13 in the tibial articular surface 12 to be repaired. On the distal side of the tibia 10, a nerve bundle 16 is located. As described herein, the system and method according to one embodiment of the present disclosure may be configured to avoid damaging the nerve bundle when forming the excision site(s).

For illustrative purposes, the following will describe a system and method for preparing an implant site comprising three partially overlapping truncated cylindrical excision sites and an implant configured to fit therein. As may be appreciated, the system and method according to the present disclosure may be used to form an implant site having greater than or fewer than three partially overlapping truncated cylindrical excision sites. As will be evident from the following description, the truncated cylindrical excision sites may be formed by drilling along the anterior-posterior plane (i.e., from an anterior face of the tibia 10 and extending generally towards the posterior face of the tibia 10).

Figure 2:
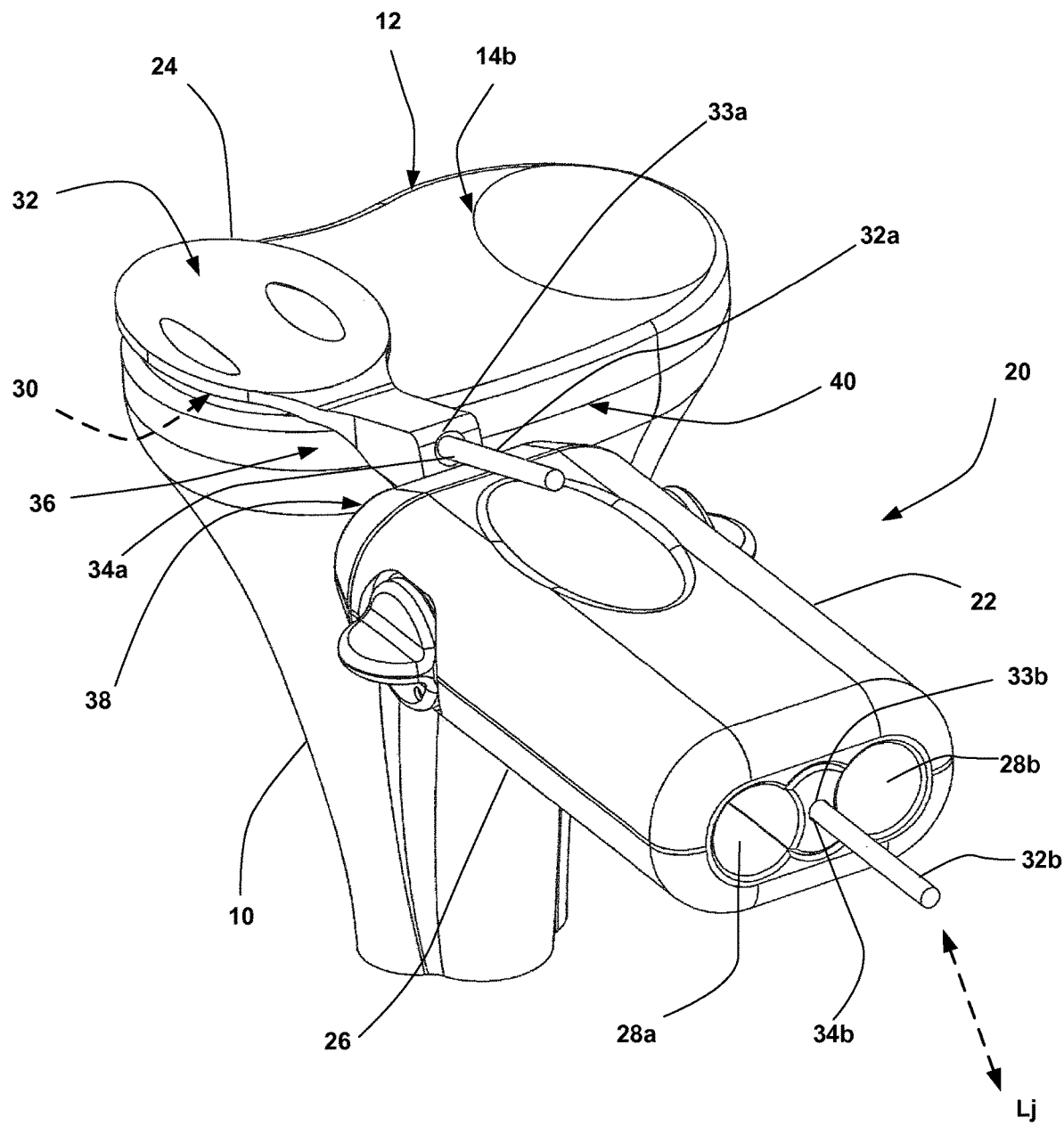
FIG. 2 is a perspective view illustrating one embodiment of a drill guide coupled to the tibia consistent with the present disclosure.

Turning now to FIG. 2, one embodiment of a first guide 20 secured to the tibia 10 is generally illustrated consistent with the present disclosure. The first guide 20 may include a jig 22 and a spoon 24. The jig 22 may include a body portion 26 defining two excision passageways 28a, 28b. As explained herein, the excision passageways 28a, 28b may each define a generally cylindrical core pathway for a drill bit which may be used to form a first and a second truncated cylindrical excision site on the tibial articular surface 12. As shown, the first and the second excision passageways 28a, 28b may be offset relative to each other (i.e., the first and the second excision passageways 28a, 28b may be separated by a distance generally perpendicular to the longitudinal axes of the first and the second excision passageways 28a, 28b such that the first and the second truncated cylindrical excision sites formed in the articular surface 12 do not overlap as described herein).

The position of the jig 22 (and in particular, the excision passageways 28a, 28b) may be set based on, at least in part, the spoon 24. In particular, the spoon 24 may include a generally convex base portion 30 having a surface contour substantially corresponding to the curvature of the concaved surface 14a being repaired (e.g., the concaved surface 14a which has the defect 13). The upper portion 32 of the spoon 24 may have a generally concaved surface (e.g., generally corresponding to the curvature of the concaved surface 14a being repaired). The spoon 24 may have a cross-sectional thickness configured to facilitate advancement of the spoon 24 between the tibial articular surface 12 and the femoral condyles (not shown). For example, the cross-sectional thickness of the spoon 24 may be selected to provide sufficient rigidity to align the jig 22 relative to the tibial articular surface 12 (and in particular, the defect 13 on the concaved surface 14a) while also minimizing the required separation between the tibia 10 and the femur.

The spoon 24 may be an integral component of the jig 22 (e.g., a unitary or single one-piece structure) or may be configured to be releasably coupled to the jig 22. For example, the spoon 24 may include an arm portion 36 configured to extend generally outwardly from a distal face 38 (e.g., a bone facing surface) of the jig 22. The size and shape of the arm portion 36 may be configured to allow a portion of the distal face 38 to be disposed proximate to the perimeter (e.g., proximate to the meniscus 40) when the spoon 24 is disposed on the concaved surface 14a such that the generally cylindrical core pathways associated with the first and second excision passageways 28a, 28b partially overlap with the tibial articular surface 12.

In practice, the first guide 20 may be positioned relative to the defect 13 on the concaved surface 14a by advancing the spoon 24 between the tibial articular surface 12 and the femur such that the base portion 30 of the spoon 24 is disposed over at least a portion of the defect 13 on the tibial articular surface 12. The spoon 24 may be advanced until the distal face 38 of the jig 22 generally abuts against a portion of the tibia 10 (e.g., proximate to the meniscus 40). The size and shape of the base portion 30 as well as the arm portion 36/distal face 38 may be configured to generally center the spoon 24 within the concaved surface 14a.

Once the spoon 24 is positioned over the defect 13, the spoon 24 and the jig 22 may be secured to the tibia 10 using one or more pins 32 or the like extending through one or more locking passageways 34 in the spoon 24 and/or the jig 22. For example, the spoon 24 may include a spoon locking passageway 34a extending through a portion of the spoon 24 (e.g., the arm portion 36) configured to align a pin 32a into the tibial bone beneath the tibial articular surface 12. Alternatively (or in addition), the jig 22 may include a jig locking passageway 34b extending through a portion of the body 26 configured to align a pin 32b into the tibial bone beneath the tibial articular surface 12. While two pins 32a, 32b are shown, it should be appreciated that the first guide 20 may be secured using greater than or fewer than two pins 32a, 32b.

The pins 32a, 32b may include depth feature 33a, 33b configured to control the depth of the pins 32a, 32b in the bone 10 (i.e., to prevent the pins 32a, 32b from being set too deep or too shallow into the bone 10). The depth feature 33a, 33b may comprise an indicia (e.g., but not limited to, a laser marking, groove, or the like) which may be aligned with the proximal end of the passageways 34a, 34b. Pin 32a may extend a smaller distance into the tibia 10 compared to pin 32b.

Figure 3:
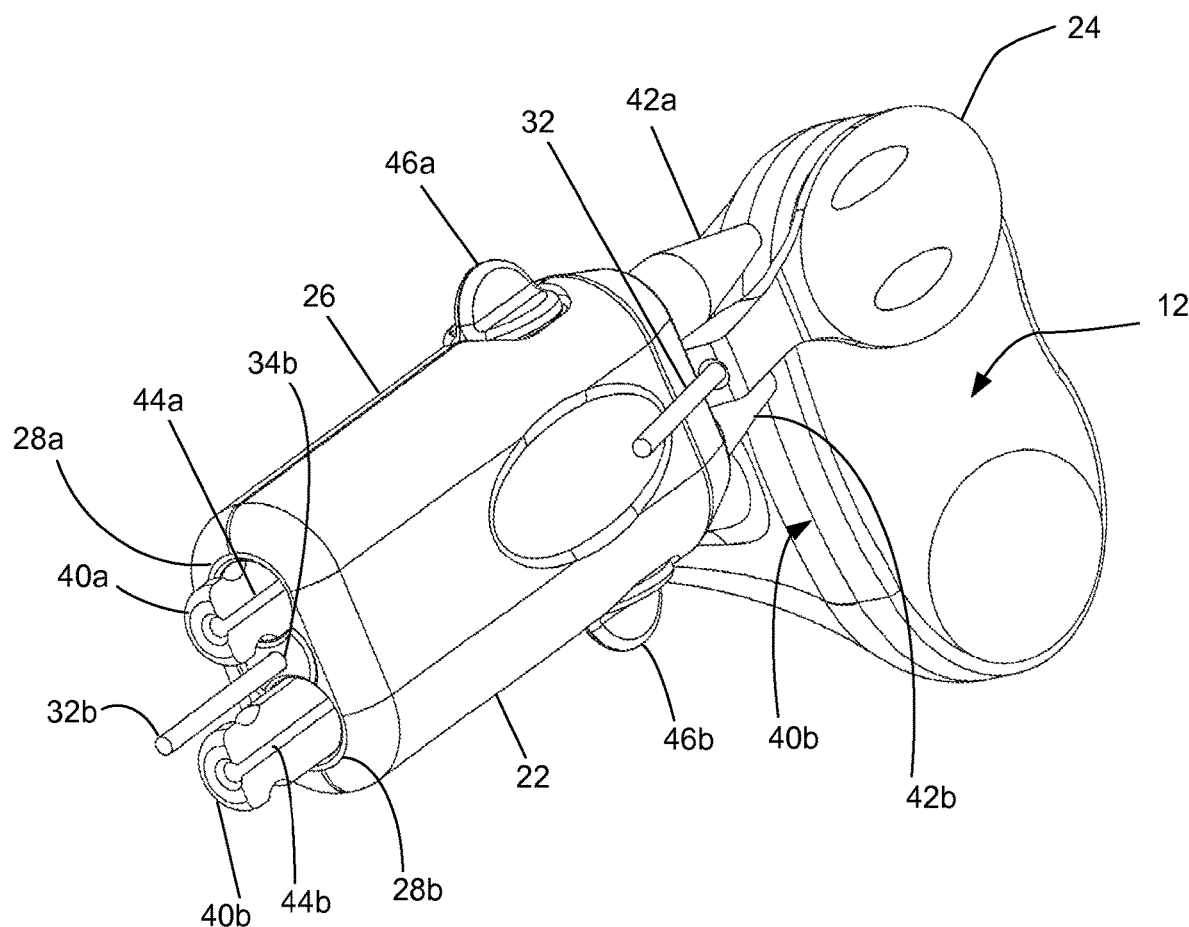
FIG. 3 is a perspective view illustrating dowels advanced within the drill guide consistent with the present disclosure.

Turning now to FIG. 3, the first guide 20 may optionally be secured to the tibia 10 by advancing one or more dowels or bushings 40a, 40b against the bone 10. For example, a first and a second dowel 40a, 40b may be advanced through the first and second excision passageways 28a, 28b, respectively. One or more of the dowels 40a, 40b may feature a tapered tip 42a, 42b and a longitudinally disposed passageway 44a, 44b (a proximal end of the dowels 40a, 40b is shown in cross-section to better illustrate the passageway 44a, 44b). The dowels 40a, 40b may be advanced through the passageways 28a, 28b until the tapered tip 42a, 42b engages against (e.g., abuts) a portion of the tibia 10 (e.g., proximate to the meniscus 40). Once the dowels 40a, 40b abut the tibia 10, the dowels 40a, 40b may be locked into position relative to the jig 22 using locking fasteners 46a, 46b. The locking fasteners 46a, 46b may include, but are not limited to, a set screw, biased tab, ratchet mechanism, or the like.

Figure 4:
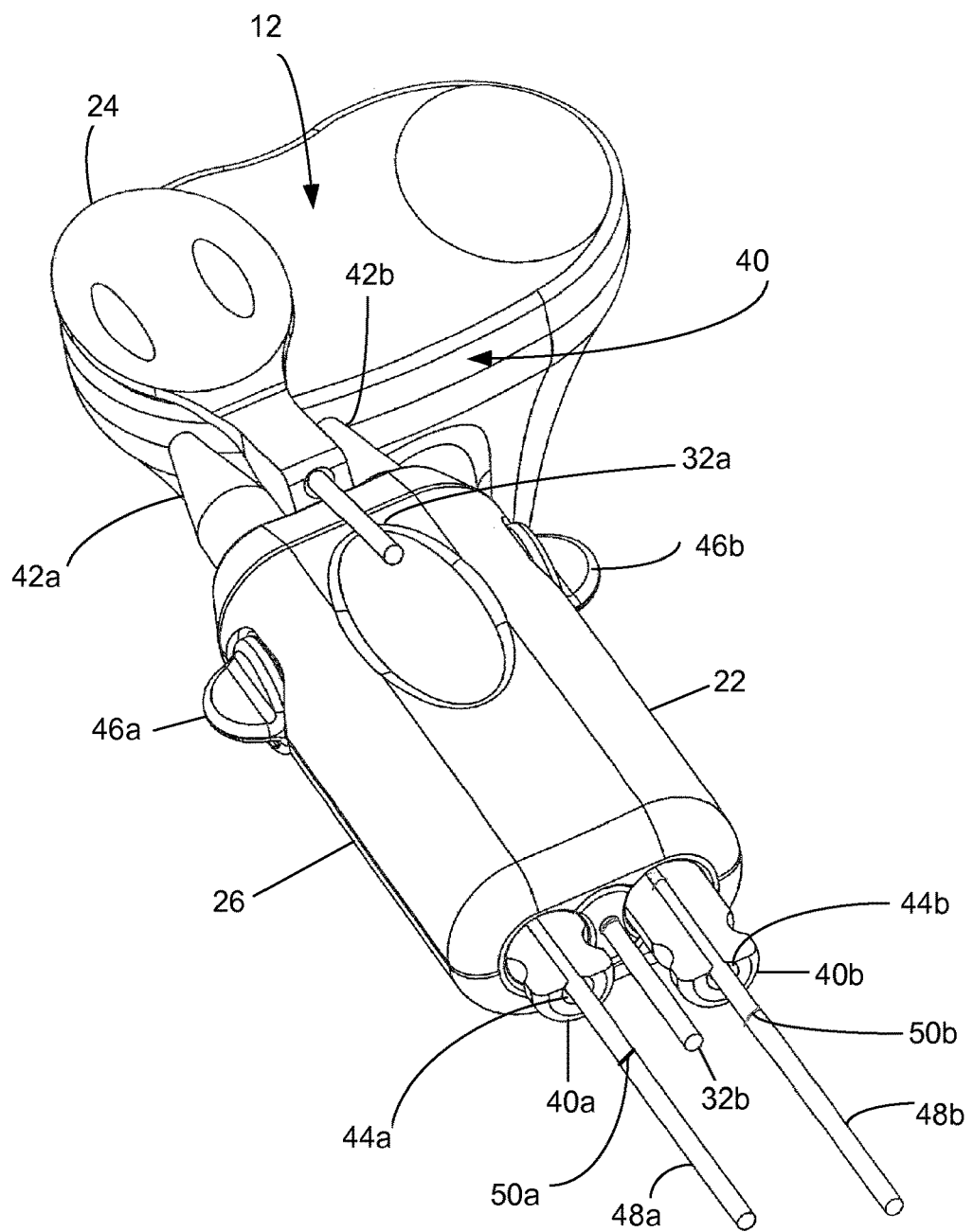
FIG. 4 is a perspective view illustrating pin advanced within the dowels in the drill guide consistent with the present disclosure.

Alignment pins 48a, 48b may be advanced through the passageways 44a, 44b in the dowels 40a, 40b and into the tibia 10 as generally illustrated in FIG. 4. Similar to the pins 34a, 34b, the alignment pins 48a, 48b may include a depth feature 50*a*, 50*b* configured to control the depth of the alignment pins 48*a*, 48*b* into the bone 10 (i.e., to prevent the alignment pins 48*a*, 48*b* from being set too deep or too shallow within the bone 10). The depth feature 50*a*, 50*b* may comprise an indicia (e.g., but not limited to, a laser marking, groove, or the like) which may be aligned with the proximal end of the passageway 44*a*, 44*b* in the dowels 40*a*, 40*b*.

Figure 5:
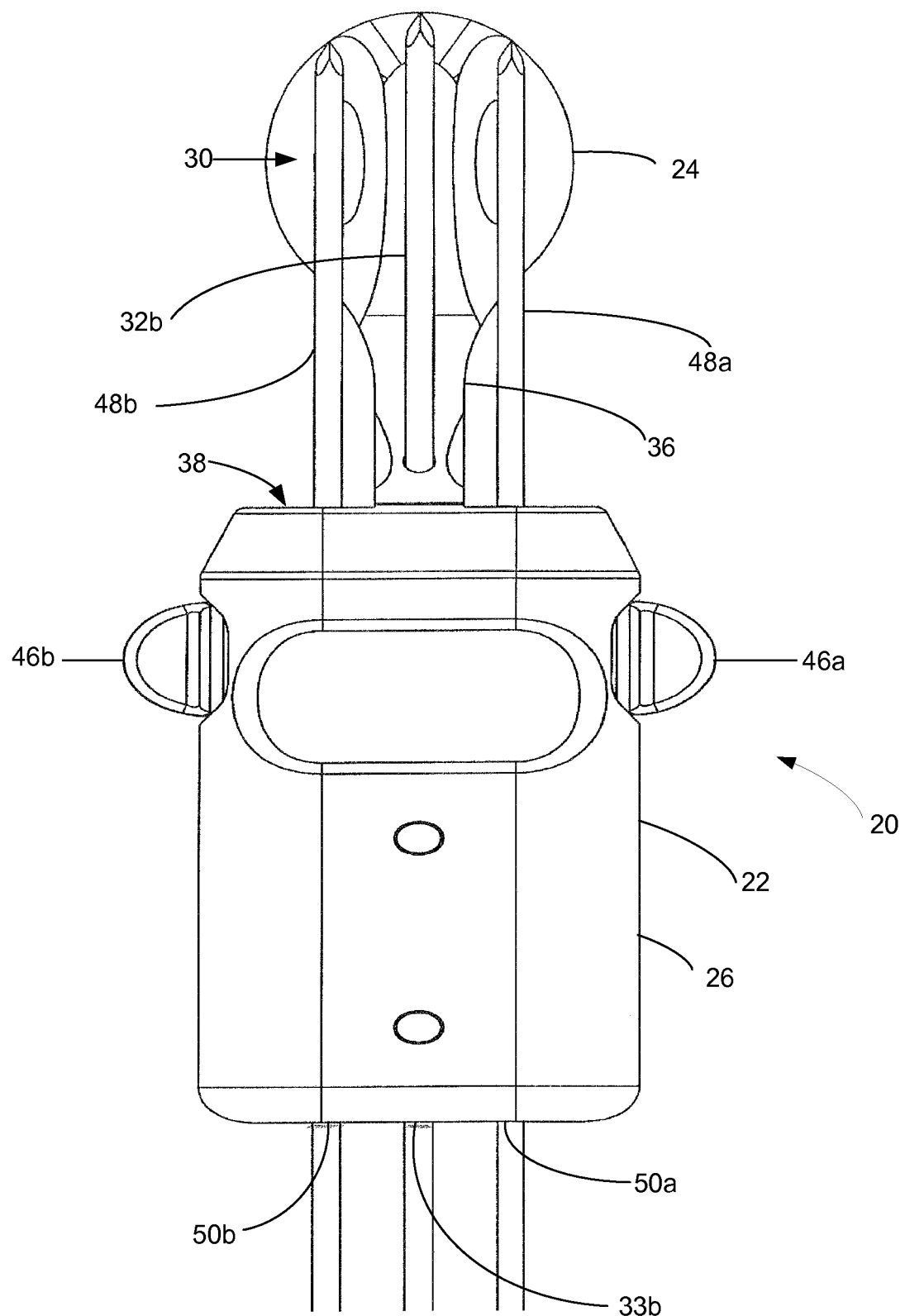
FIG. 5 is a bottom plan view of one embodiment of a drill guide as generally shown in FIG. 4 consistent with the present disclosure.

FIG. 5 is a bottom plan view of the first guide 20 generally illustrating one embodiment of the position of the alignment pins 48*a*, 48*b* as well as pin 32*b* relative to the spoon 24. As can be seen, depth features 50*a*, 50*b*, 33*b* are generally aligned with the respective passageways 44*a*, 44*b*, 34*b* such that the distal ends of the pins 48*a*, 48*b*, 32*b* are generally aligned with the distal perimeter of the spoon 24. As such, the distal ends of the pins 48*a*, 48*b*, 32*b* do not extend beyond the tibial bone 10. It should be appreciates, however, that the position of the distal ends of the pins 48*a*, 48*b*, 32*b* may be disposed shallower (i.e., closer towards the first guide 20).

Figure 6:
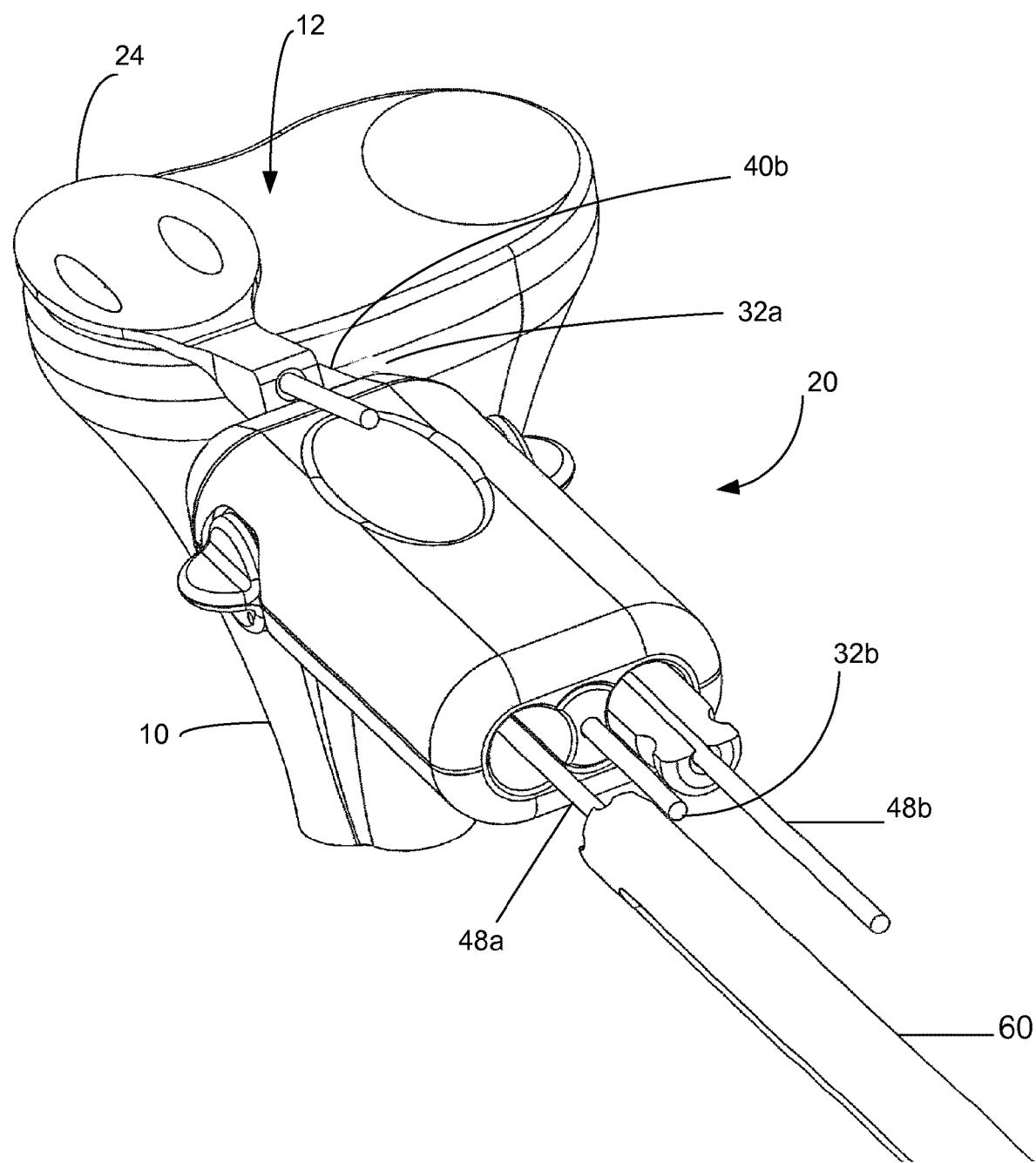
FIG. 6 is a perspective view illustrating a drill bit advanced into the drill guide consistent with the present disclosure.

Once the first guide 20 is secured to the tibia 10, a first and a second truncated cylindrical excision site may be formed in the tibial articular surface 12 and/or bone 10. The first and second truncated cylindrical excision sites may correspond to a projection of the cylindrical core pathways defined by the excision passageways 28*a*, 28*b* intersecting with the tibial articular surface 12 and/or bone 10. For example, a dowel 40*a* may be removed from the excision passageway 28*a*, leaving the pin 48*a* remaining as generally illustrated in FIG. 6. A cannulated drill 60 may then be advanced over the pin 48*a* and through the excision passageway 28*a* to form a first truncated cylindrical excision site. While dowel 40*a* is shown removed, the order in which the dowels 40*a*, 40*b* are removed may be altered.

Figure 7:
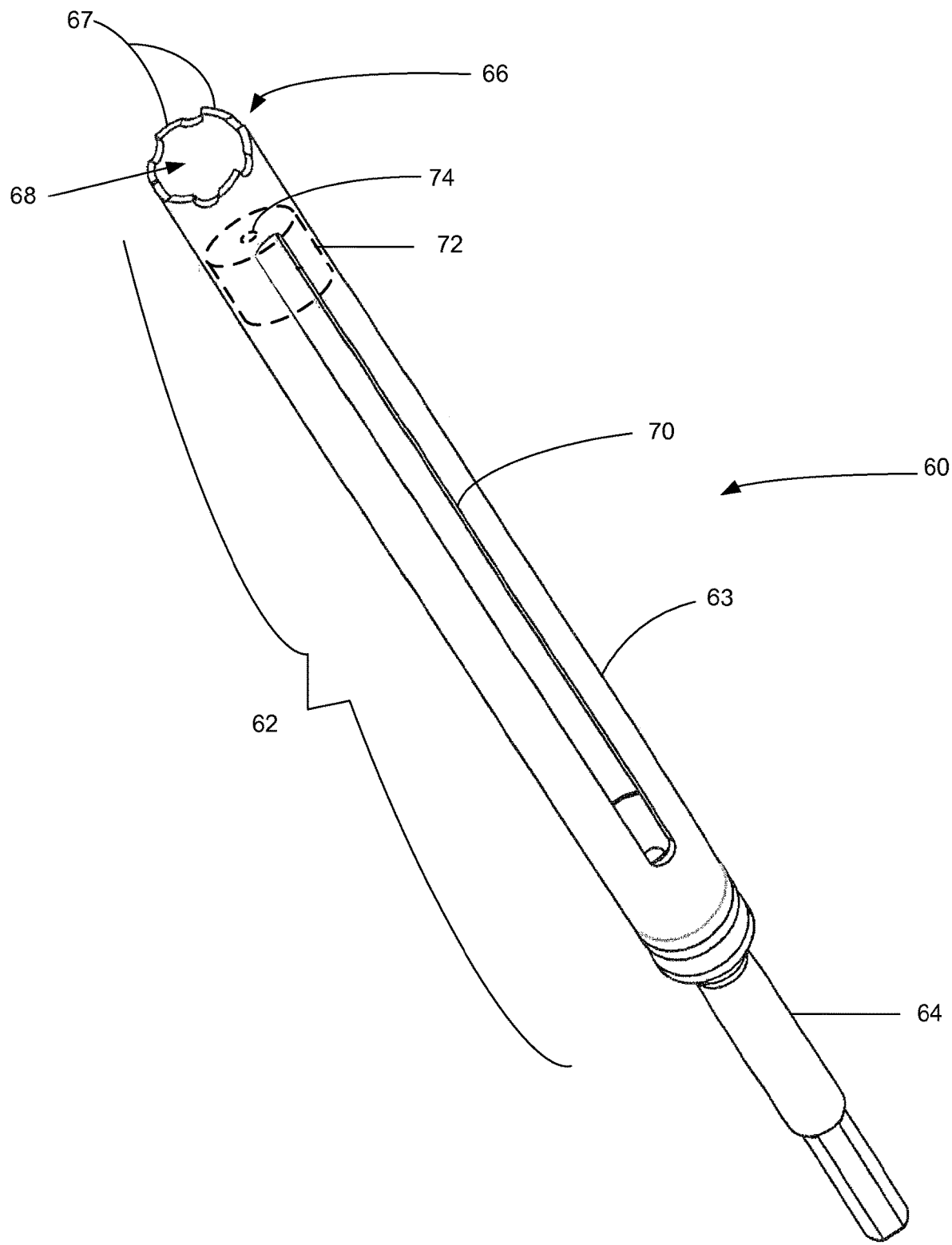
FIG. 7 is a perspective view of one embodiment of a drill bit consistent with the present disclosure.

One embodiment of a cannulated drill 60 is generally illustrated in FIG. 7. The cannulated drill 60 may feature a core drill bit 62 and optionally a shank portion 64. The shank portion 64 may include a multi-faceted proximal end configured to be secured to a drill (e.g., a hand drill, electric drill, pneumatic drill or the like). Alternatively, a proximal end of the core drill bit 62 may be directly coupled to the drill.

The core drill bit 62 may include a cutting surface 66 (for example, comprising a plurality of cutting teeth 67) disposed about a distal end of the barrel 63. The cutting surface 66 may be evenly disposed around the generally circular distal end of the barrel 63. The barrel 63 may include an outer diameter substantially corresponding to the inner diameter of the excision passageway 28*a*. For example, the core drill 62 may have an outer diameter selected from the range of 8-12 mm, for example, 10-11 mm. The barrel 63 may define a core cavity 68 configured to receive the removed portion of the tibial articular surface 12 and bone 10. As may be appreciated, the only portion of the tibial articular surface 12 and bone 10 that is cut by the core drill bit 60 corresponds to the thickness of the cutting surface 66, which itself is a function of the wall thickness of the barrel 63. As such, these thicknesses may be selected to remove the least amount of material while also providing the necessary rigidity and/or strength to the core drill bit 60.

The core drill bit 62 may optionally feature one or more windows 70 disposed along the length of the barrel 63. The window 70 may allow air, fluid, and cutting chips to exit the barrel 63. In addition, the window 70 may also allow the user to align the core drill bit 62 with the first guide 20 and/or pins to control the depth of the excision site (i.e., the length of the excision site as measured across the tibial articular surface 12). For example, a proximal end of the window 70 may be generally aligned with the opening on the excision passageway 28*a* to control the depth of the resulting excision site.

The core drill bit 62 may also optionally include a centering bearing 72 configured facilitate alignment of the core drill bit 62 as the core drill bit 62 is advanced into the tibial articular surface 12 and bone 10. The centering bearing 72 may be translatably disposed along the longitudinal axis of the core drill bit 62 and may include a passageway 74 configured to receive the pin 48*a*. For example, the centering bearing 72 may be initially located near the distal end of the barrel 62. As the core drill bit 62 is advanced within the excision passageway 28*a*, the pin 48*a* may be received in the passageway 74 and the centering bearing 72 may translate towards the proximal end as the core is received in the passageway 74.

As the drill bit 60 is advanced through the excision passageway 28*a* in the first guide 20, a portion of the cutting surface 66 may engage the tibial articular surface 12 and/or the bone 10, thereby forming a truncated cylindrical excision site. Once the drill bit 60 has been advanced through the excision passageway 28*a* to create the first excision site, the second truncated cylindrical excision site may be formed. For example, the second dowel 40*b* may be removed and a second drill bit 60 may be advanced through the second excision passageway 28*b* in a manner similar to that described herein. The first and second drill bits 60 may have the same or different outer diameters.

As discussed herein, the first and the second excision passageways 28*a*, 28*b* may be offset relative to each other. Put another way, the first and the second excision passageways 28*a*, 28*b* may be separated by a distance generally perpendicular to the longitudinal axes of the first and the second excision passageways 28*a*, 28*b* such that the first and the second truncated cylindrical excision sites do not overlap.

Figure 8:
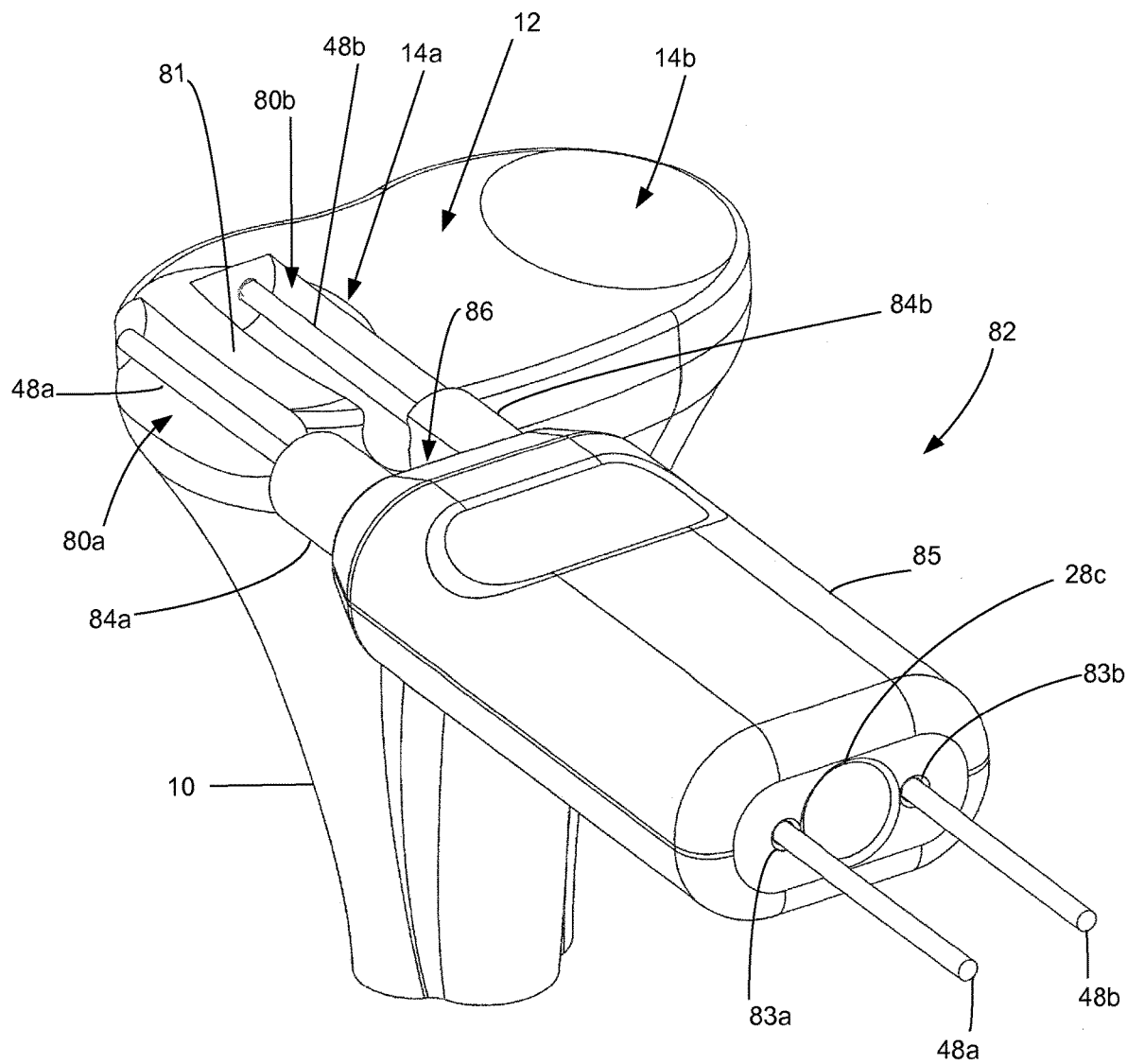
FIG. 8 illustrates one embodiment of a first and second excision site formed on the tibial articular surface and a second drill guide coupled thereto consistent with the present disclosure.

FIG. 8 generally illustrates one embodiment of the first and the second truncated cylindrical excision sites 80*a*, 80*b* corresponding to the drill bit 60 and the first and the second excision passageways 28*a*, 28*b*. As can be seen, a center section 81 of articular surface 12/bone 10 remains separating the first and the second truncated cylindrical excision sites 80*a*, 80*b*. This center section 81 may optionally be removed using second guide/jig 82.

The second guide 82 may comprise one or more alignment passageways 83*a*, 83*b* as well as a third excision passageway 28*c* extending through the body portion 85. The third excision passageway 28*c* may also define a generally cylindrical core pathway for a drill bit. Once the first and the second truncated cylindrical excision sites 80*a*, 80*b* have been formed, the first guide 20 and pins 32*a*, 32*b* may be removed and pins 48*a*, 48*b* may remain secured to the bone 10. The second guide 82 may then be advanced over the pins 48*a*, 48*b* to align the second guide 82 (and in particular the third excision passageway 28*c*) relative to the articular surface 12 and the center section 81. Optionally, the second guide 82 may feature protrusions 84*a*, 84*b* configured to be at least partially received in the first and the second truncated cylindrical excision sites 80*a*, 80*b* to further align and secure the position of the second guide 82 and the third excision passageway 28*c* relative to the articular surface 12/center section 81. The second guide 82 may therefore be advanced along the pins 48*a*, 48*b* and the protrusions 84*aa*, 84*b* may be received into the first and the second truncated cylindrical excision sites 80*a*, 80*b* until at least a portion of the distal face 86 of the second guide 82 generally abuts against the bone 12 and a projection of the third core pathway associated with the third excision passageway 28c partially intersects with the center section 81.

Figure 9:
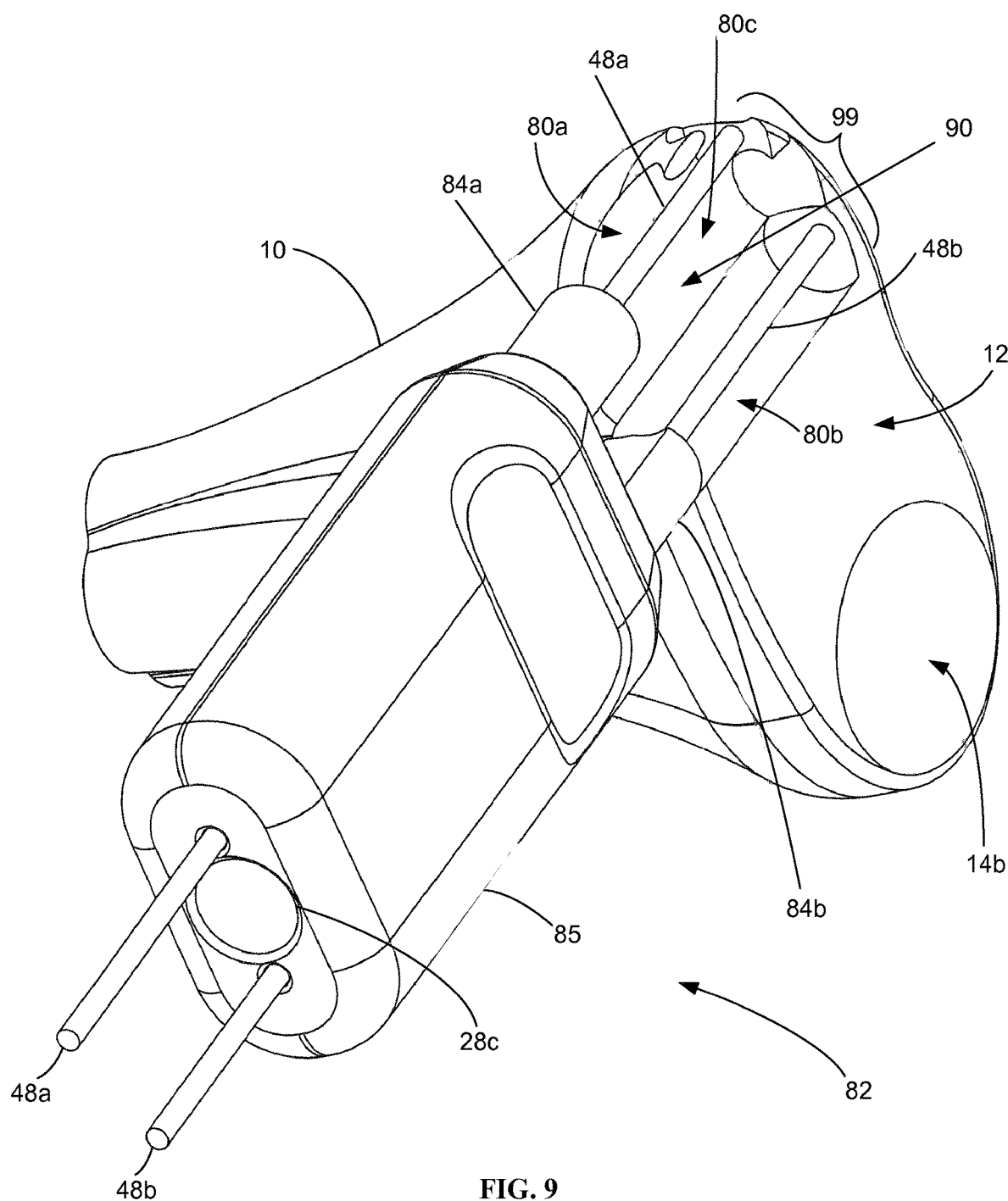
FIG. 9 is a perspective view of one embodiment of a third excision site formed on the tibial articular surface using the second drill guide consistent with the present disclosure.

Once the second guide 82 is aligned with the first and second excision sites 80a, 80b and the pins 48a, 48b, a third drill 60 may be advanced through the third excision passageway 28c extending through the body 85 to remove the center section 81 and form the third truncated cylindrical excision site 80c as generally illustrate in FIG. 9. The third excision passageway 28c may be configured to align the third drill 60 such that the resulting third truncated cylindrical excision site 80c partially overlaps with the first and the second truncated cylindrical excision sites 80a, 80b. For example, the third excision passageway 28c may have a diameter which would partially overlap with the first and the second excision passageways 28a, 28b if the three excision passageways 28a-28c were transposed on each other and aligned with the pins 48a, 48b.

The resulting implant site may therefore comprise the first, second, and third truncated cylindrical excision sites 80a-80c wherein the first and the second truncated cylindrical excision sites 80a, 80b partially overlap with the third truncated cylindrical excision site 80c. The truncated cylindrical excision sites 80a-80c may be centered/revolved around the pins 48a, 48b, 32b and may extend along the articular surface 12 generally along the anterior-posterior plane. For example, the truncated cylindrical excision sites 80a-80c may extend from the anterior face of the tibial articular surface 12 generally towards the posterior face. The implant site may therefore include a base portion 90 comprising three overlapping truncated cylindrical extensions or scallops defined by the three excision passageways 28a-28c. The resulting implant site therefore may generally eliminate/reduce the occurrence of 90 degree cuts and therefore more evenly distribute loads/forces to the bone 10 compared a traditional 90 degree notch cut.

The truncated cylindrical excision sites 80-80c have been illustrated extending partially across the tibial articular surface 12 (i.e., one or more of the truncated cylindrical excision sites 80-80c do not extend completely across the articular surface 12 thus leaving a portion 99 of the tibial articular surface 12 and/or bone 10 remaining). This embodiment may be particularly beneficial since it further minimizes the potential for accidentally damaging the nerve bundle. However, the system and method according to the present disclosure may also allow for one or more of the truncated cylindrical excision sites 80a-80c to extend completely across the articular surface 12 as generally illustrate in FIG. 10. In particular, the system and method according to the present disclosure may be able to accurately enough form the truncated cylindrical excision sites 80a-80c to minimize the potential of damaging the nerve bundle to an acceptable level.

While the system and method has been described having a first and a second guide 20, 82, the system and method may utilize a single guide. For example, the first guide 20 may include alignment dowels (not shown) configured to be advanced and/or secured within the first and second excision passageways 28a, 28b. The alignment dowels may include protrusions 84a, 84b configured to engage the first and second truncated excision sites 80a, 80b as generally described herein. In addition, the guide 20 may include a third excision passageway 28c extending generally along the locking passageway 34b (which itself may be formed in a removable bushing). The alignment dowels may have an outer shape such that the third excision passageway 28c defines a generally cylindrical core pathway for the drill 60.

Figure 11:
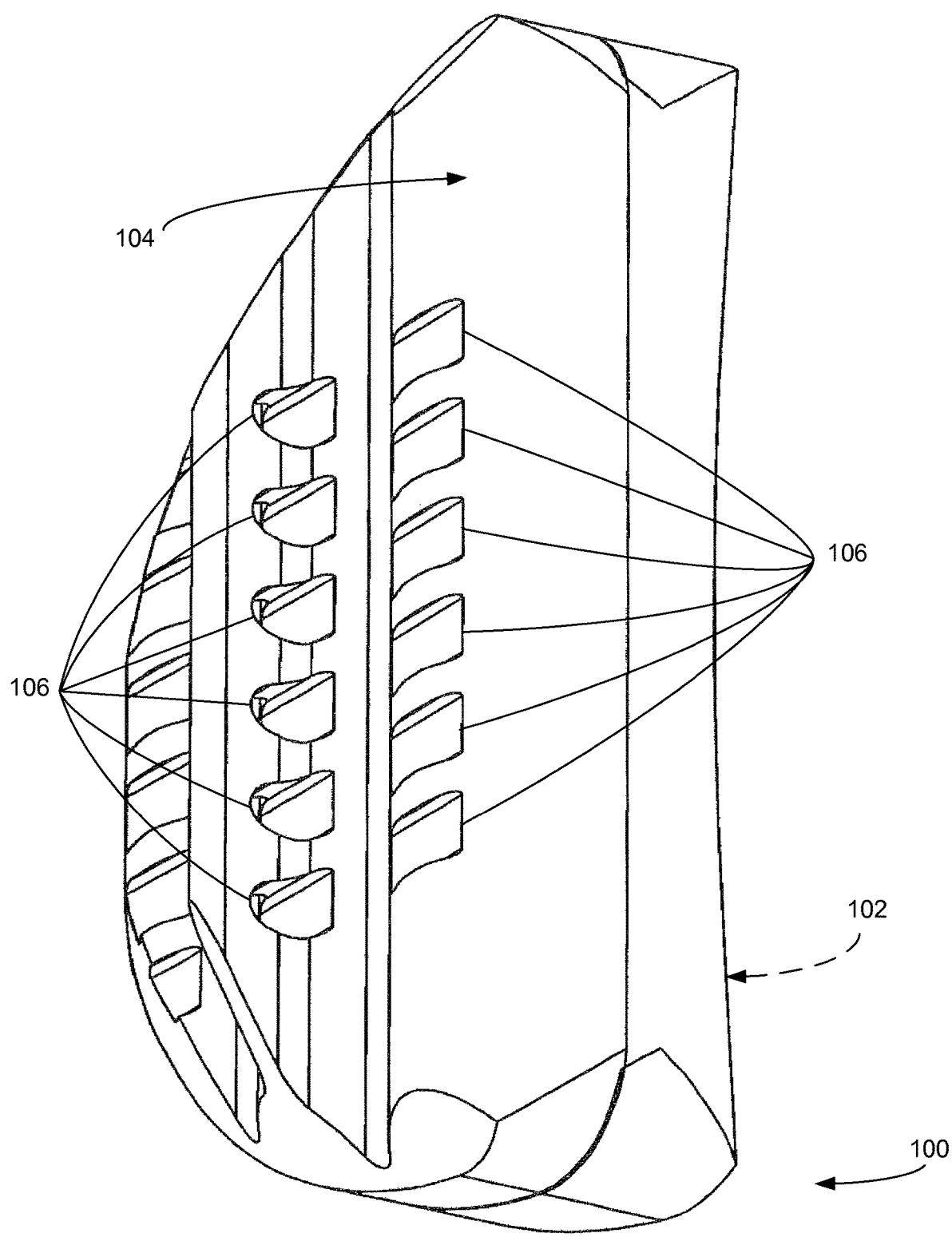
FIG. 11 is a perspective bottom view of one embodiment of an implant consistent with the present disclosure.

Turning now to FIG. 11, one embodiment of an implant 100 consistent with the present disclosure is generally illustrated. The implant 100 may comprise a load bearing surface 102 and a bone facing or distal surface 104. The load bearing surface 102 may have a surface contour/geometry substantially corresponding to the contour/geometry of the removed tibial articular surface 12 proximate the defect 13. The contour/geometry of the load bearing surface may be based on a plurality of measurement take of the patient's tibial articular surface 12, for example, as described in U.S. patent application Ser. No. 10/373,463, filed on Feb. 24, 2003, entitled System and Method for Joint Resurface Repair, which is fully incorporated herein by reference.

The bone facing surface 104 may have an overall contour/geometry generally corresponding to the contour/geometry of the base portion 90 of the three truncated cylindrical excision sites 80a-80c and the removed bone 10. Optionally, the bone facing surface 104 may include one or more relief cavities, pockets and/or cross-cuts 106 configured to enhance securing the implant 100 to the bone 10 within the truncated cylindrical excision sites 80a-80c. The relief cavities 106 may be configured to allow bone regrowth around a portion of the implant 100 and/or promote cement adhesion. As shown, the implant 100 may comprise a generally unitary structure (i.e., the implant 100 may be a solid, one-piece component). For example, the implant 100 may be made from ultra-high molecular weight polyethylene (UHMWPE).

Figure 12:
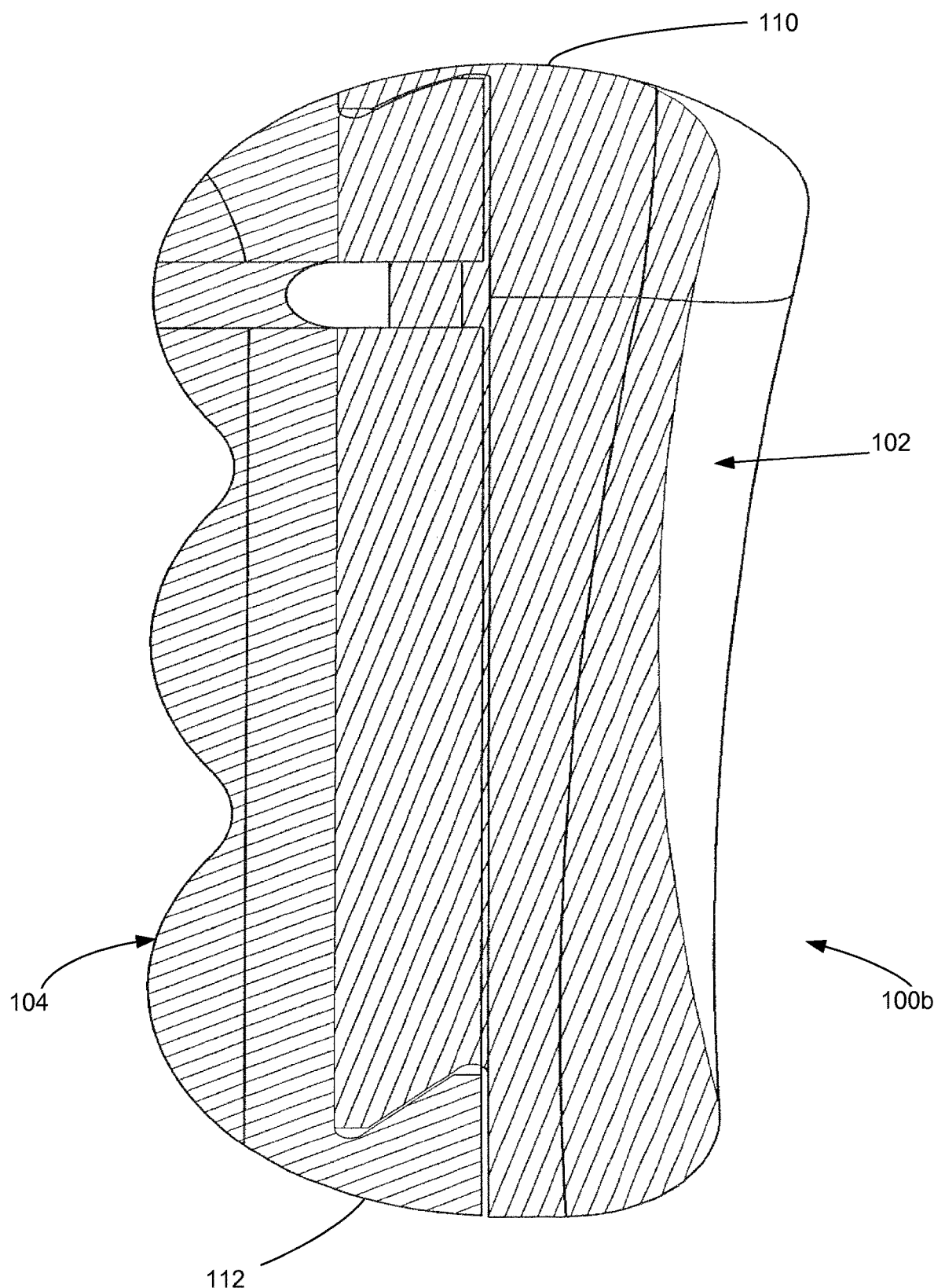
FIG. 12 is a cross-sectional side view of another embodiment of an implant consistent with the present disclosure.

Turning now to FIG. 12, a cross-sectional view of another embodiment of an implant 100b consistent with the present disclosure is generally illustrated. Implant 100b may comprise multiple portions configured to be coupled together, for example, an upper and a lower portion 110, 112. The upper portion 110 may include a load bearing surface 102 as described herein while the lower portion 112 may comprise a bone facing surface 104 as described herein. The upper and lower portions 110, 112 may be configured to be coupled together. For example, the lower portion 112 may be based on the guides 20, 82 used to form the truncated cylindrical excision sites 80a-80c while the upper portion 110 may be based on the contour/geometry of the patient's removed articular surface 12. Put another way, the lower portion 112 may be considered "generic" or common in that it is based on the guides 20, 82 rather than measurements of the patient's articular surface 12 while the upper portion 110 may be selected based specifically on measurements of the patient's articular surface 12.

Figure 13:
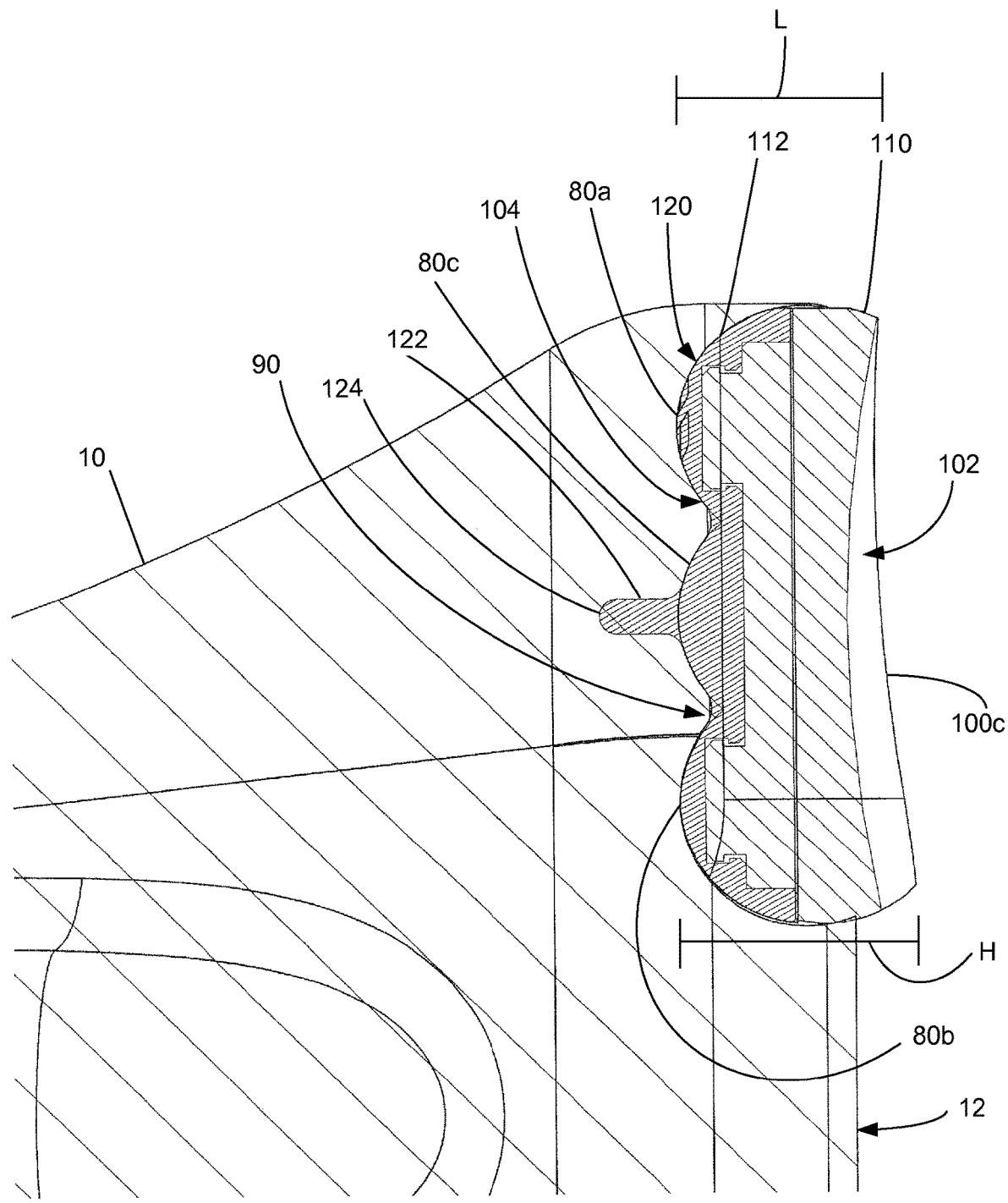
FIG. 13 is a cross-sectional view of yet another embodiment of an implant consistent with the present disclosure.

Turning now to FIG. 13, a cross-sectional view of another implant 100c is shown generally implanted within the implant site 120 formed by truncated cylindrical excision sites 80a-80c. As shown, the bone facing surface 104 of the implant 100c may be generally disposed along the base portion 90 of the truncated cylindrical excision sites 80a-80c while the load bearing surface 102 may be substantially continuous with the surrounding tibial articular surface 12 (i.e., the tibial articular surface 12 adjacent to and abutting the implant 100c). The implant 100c may optionally comprise one or more keels, tails, protrusions or the like 122. The keel 122 may extend generally downwardly from the bone facing surface 104 and away from the load bearing surface 102. The keel 122 may be configured to engage a corresponding notch 124 formed in the base portion 90 of the truncated cylindrical excision sites 80a-80c. While the implant 100c is illustrated having an upper and a lower portion 110, 112, the implant 100 as illustrated in FIG. 11 may optionally include one or more keels 122. The keel 122 may be an integral component of the implant 100 or the lower portion 112 or alternatively may be a separate component coupled thereto.

As may be appreciated from FIGS. 11-13, an implant consistent with at least one embodiment of the present disclosure may have a load bearing surface 102 which is non-planar. While traditional tibial implants have had a generally planar or flat load bearing surface, an implant consistent with at least one embodiment of the present disclosure may have a concaved geometry which may better approximate the geometry of the patient's removed tibial articular surface 12. For example, the implant as shown in FIG. 13 may have a first side (e.g., but not limited to, a medial side) having a height L less than a height H of a second side (e.g., but not limited to, the lateral side).

Figure 10:
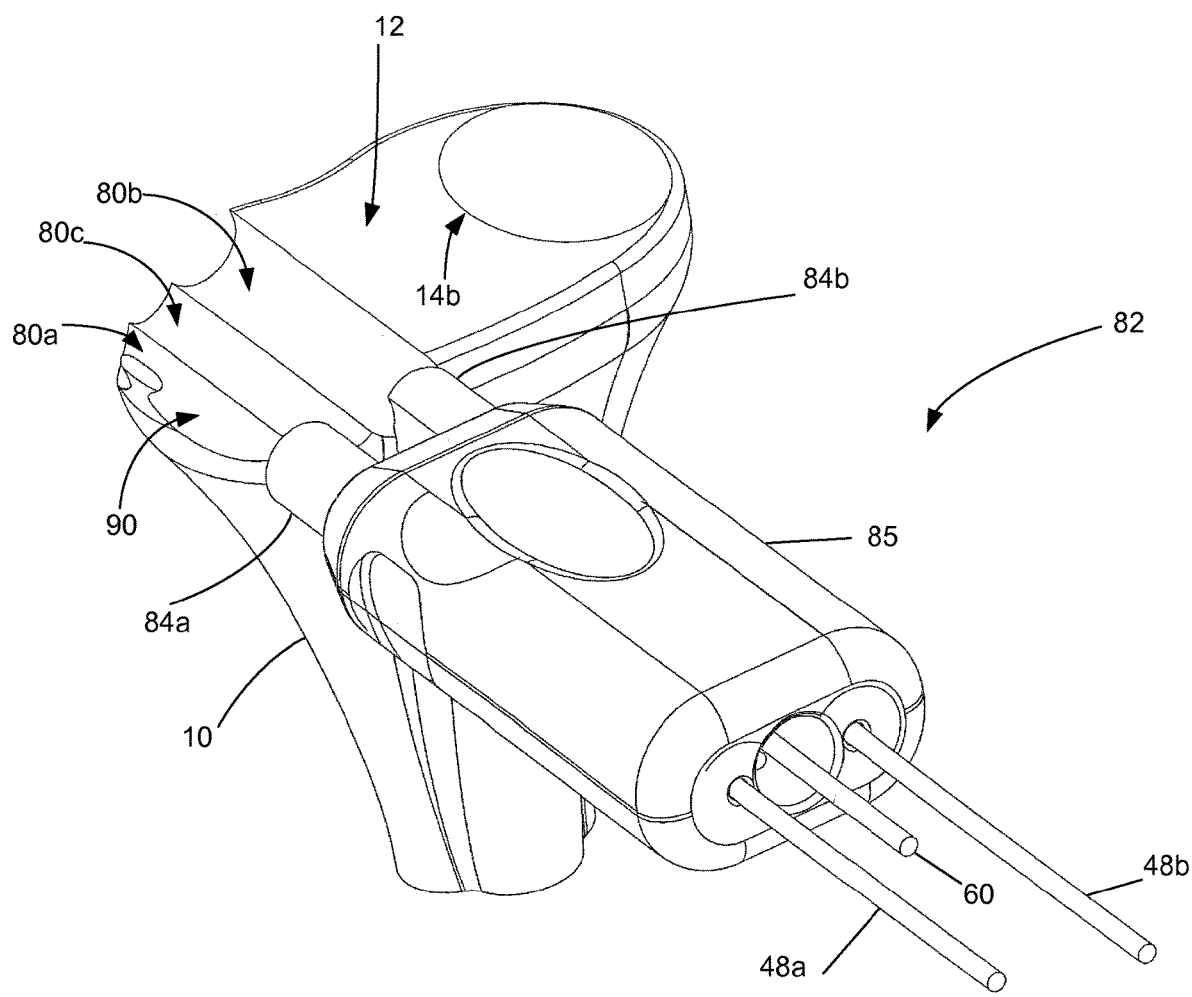
FIG. 10 is a perspective view of another embodiment of a first, second, and third excision site formed on the tibial articular surface using the first and/or second drill guides consistent with the present disclosure.
Figure 14:
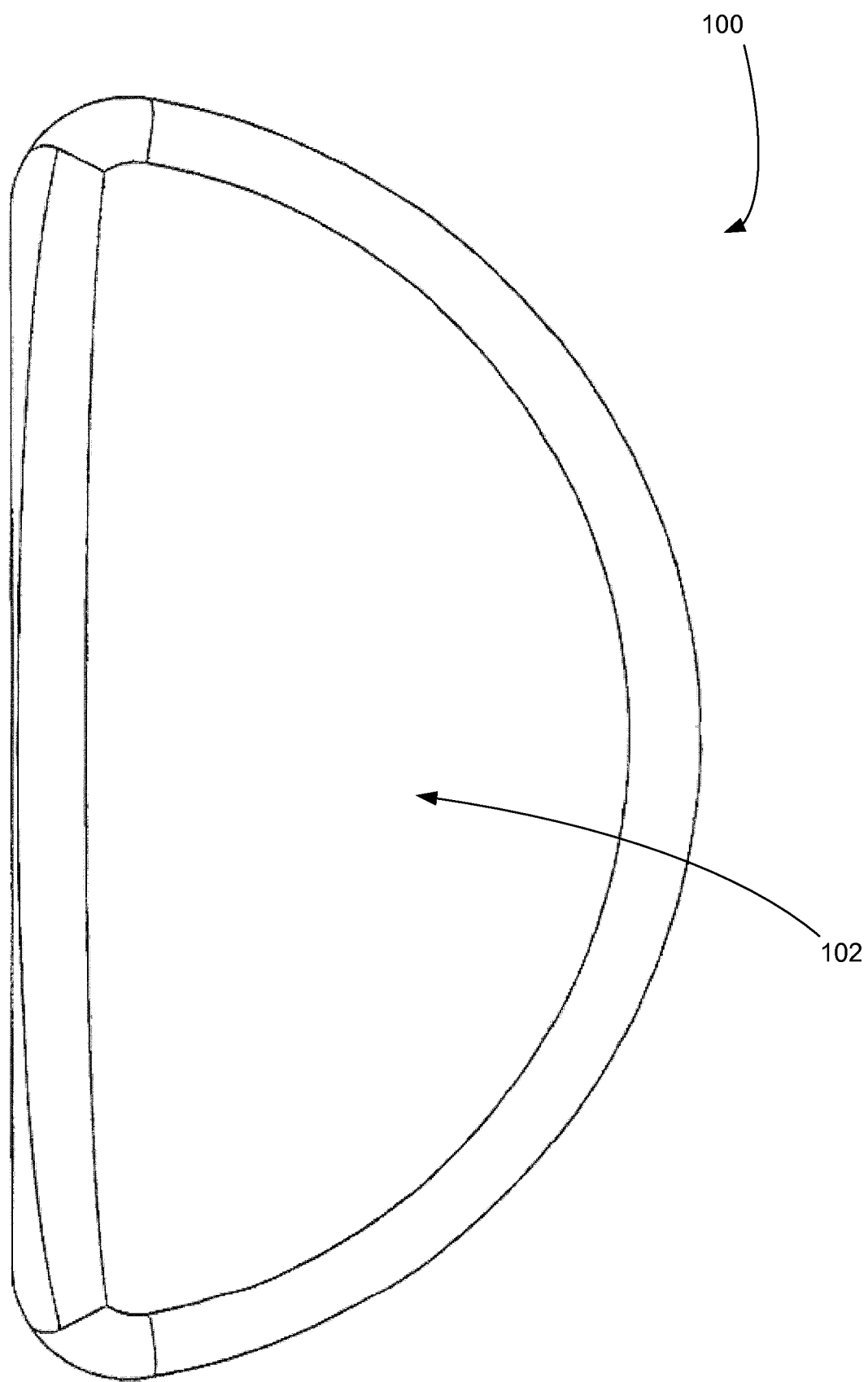
FIG. 14 is a top view of one embodiment of an implant consistent with the present disclosure.
Figure 15:
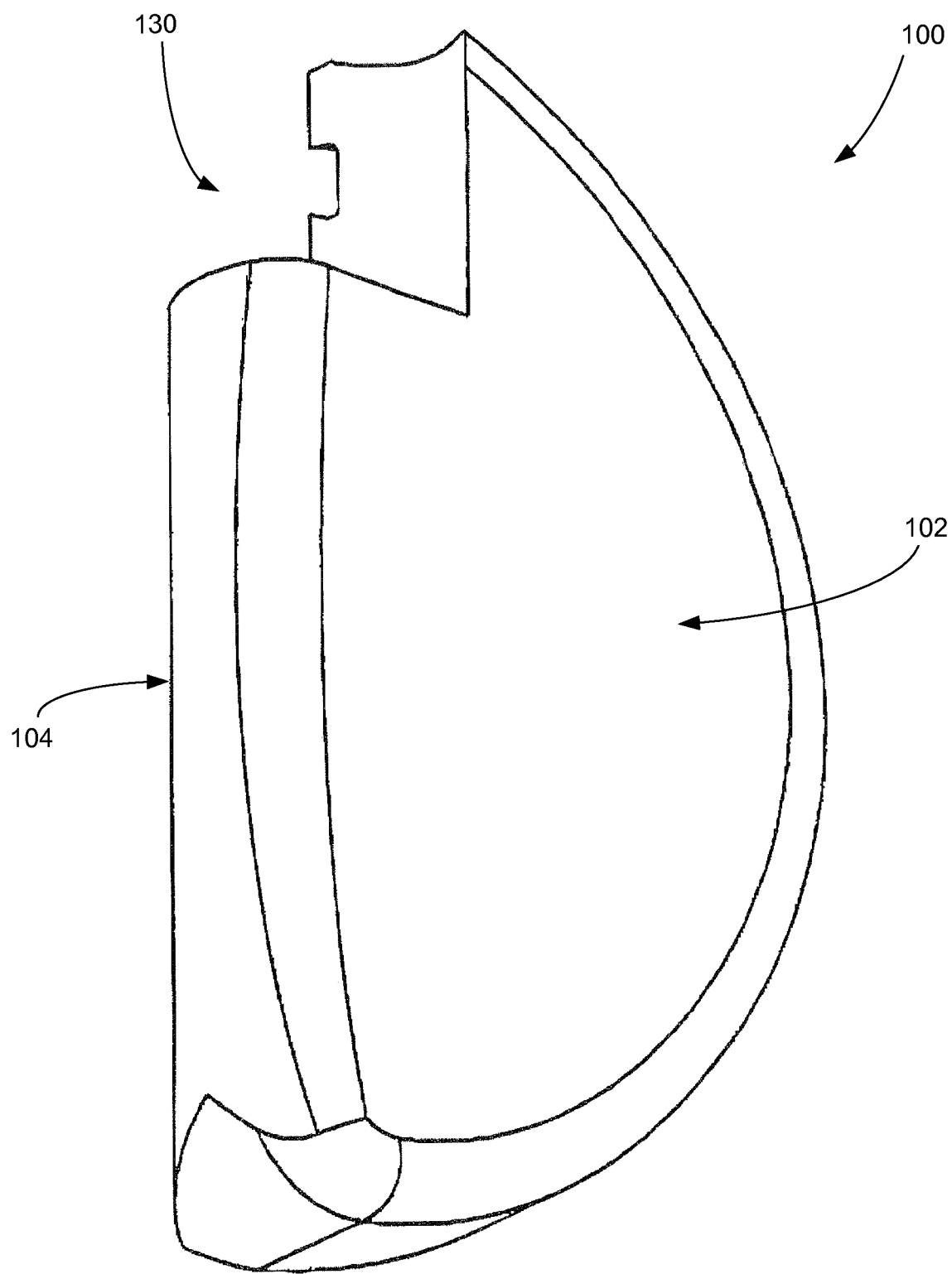
FIG. 15 is a top view of another embodiment of an implant consistent with the present disclosure.
Figure 16:
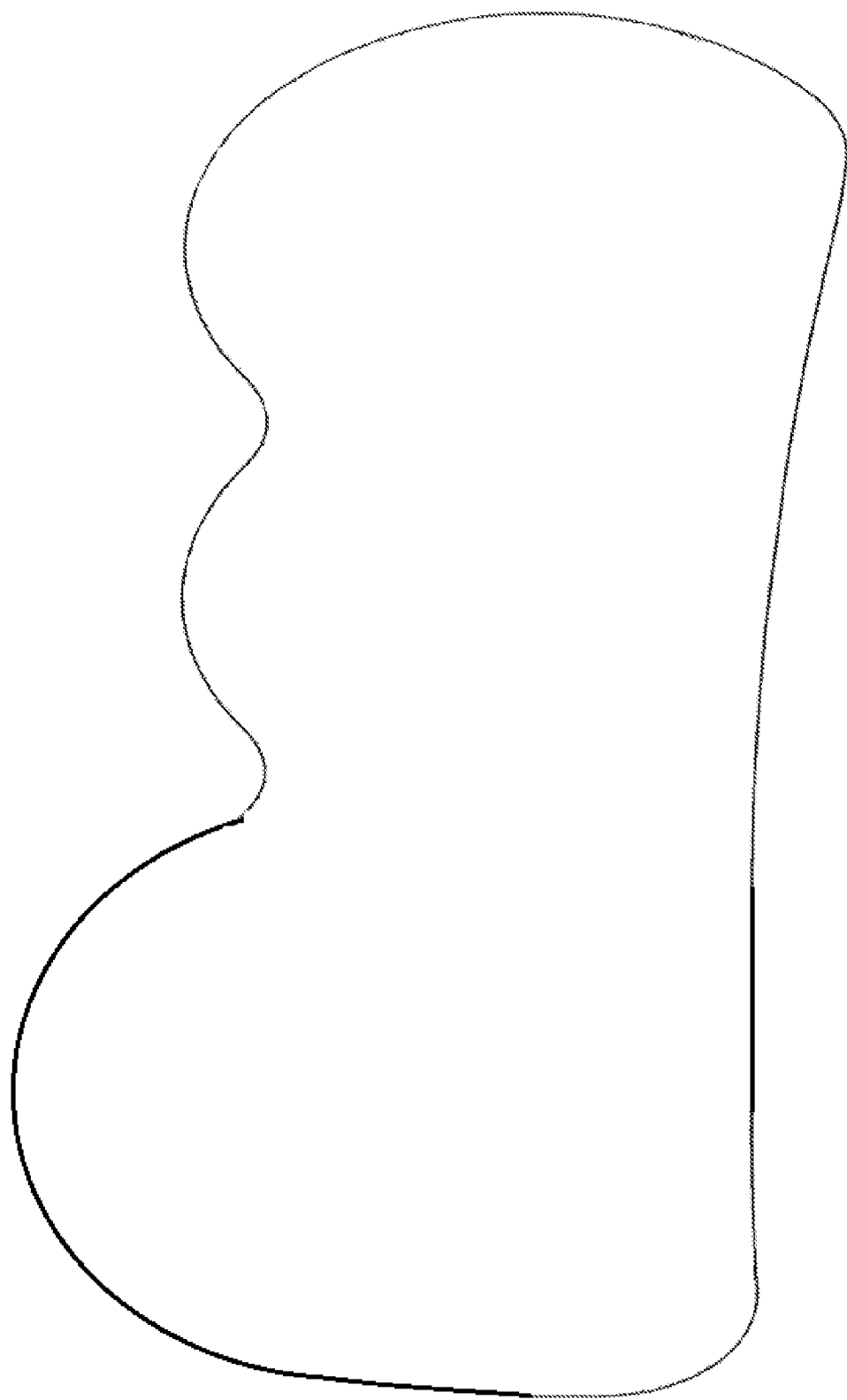
FIG. 16 is a side view of another embodiment of an implant consistent with the present disclosure.

Turning now to FIG. 14, a top view of one embodiments of the implant 100 consistent with the present disclosure is generally illustrated. When viewed from the top side (i.e., when viewing the load bearing surface 102), the implant 100 may have a generally "D" shape. This "D" shape may correspond to an implant site which extends all the way cross the anterior-posterior plane of the articular surface (e.g., as generally shown in FIG. 10). As shown in FIG. 15, the implant 100 may also have a modified or notched "D" shape. In particular, the implant 100 may include a notched region 130 which may correspond to the area 99 of the tibial articular surface 12 proximate to the posterior face of the tibia 10 which is not removed (e.g., as generally shown in FIG. 9). As discussed herein, leaving this portion 99 of the tibial articular surface 12 and/or bone 10 intact may minimize the potential of damaging the nerve bundle 16 (FIG. 1).

According to one aspect, the present disclosure features an implant resection system for preparing an implant site to replace a defect in an articular surface of a first bone. The implant resection system includes a guide configured to be coupled generally perpendicular to the first bone proximate to the defect. The guide includes a body portion defining a plurality of excision passageways. The excision passageways each define a generally cylindrical core pathway configured to extend generally perpendicular to the first bone which partially overlaps with an adjacent generally cylindrical core pathway. A projection associated with each of the plurality of the generally cylindrical core pathways defines a truncated cylindrical excision site extending through a portion of the articular surface. Each truncated cylindrical excision site partially overlaps with at least one adjacent truncated cylindrical excision site.

According to another aspect, the present disclosure features a method for preparing an implant site to replace a defect in an articular surface. The method includes securing a guide to bone proximate the defect. The guide includes a body portion defining a plurality of excision passageways. Each excision passageway defines a generally cylindrical core pathway which partially overlaps with an adjacent generally cylindrical core pathway. The method further includes advancing at least one drill through the plurality of excision passageways along the generally cylindrical core pathways to form a plurality of partially overlapping truncated cylindrical excision sites extending through the articular surface.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

Additional disclosure in the format of claims is set forth below.

What is claimed is:

1. An implant system comprising an implant for replacing only a portion of a patient's articular surface of a tibial plateau of a tibial bone, said implant including:
    a load bearing surface having a contour based on a plurality of measurements taken of the removed portion of the articular surface corresponding to an implant site in the tibial plateau of the tibial bone; and
    a bone facing surface including a first and a second truncated cylindrical protrusion extending along a length of two opposite lateral sides of said bone facing surface, respectively, said first and said second truncated cylindrical protrusion comprising arcs of circles and are defined by portions of a first and a second different cylindrical projection corresponding to said arcs of said circles,
    wherein the implant has a thickness extending between said load bearing surface and said bone facing surface that is less than a diameter of said circles and is configured such that the bone facing surface abuts against the tibial bone within the implant site and the load bearing surface is substantially continuous with the articular surface surrounding the removed portion of articular surface when the implant is received in the implant site; and
    wherein portions of the load bearing surface opposite the bone facing surface of said first and said second truncated cylindrical protrusion are disposed within said first and said second different cylindrical projection.

2. The implant system of claim 1, wherein said first and said second truncated cylindrical protrusion define a first and a second generally opposite side of said bone facing surface, respectively.

3. The implant system of claim 1, wherein said first and said second truncated cylindrical protrusion have the same diameter.

4. The implant system of claim 1, wherein said first and said second truncated cylindrical protrusion have different diameters.

5. The implant system of claim 1, wherein said first and said second truncated cylindrical protrusion are spaced apart such that said first and said second different truncated cylindrical projections do not overlap.

6. The implant system of claim 1, further comprising at least one keel extending generally downwardly from said bone facing surface generally perpendicularly from said length.

7. The implant system of claim 1, wherein said bone facing surface further comprises a plurality of relief cavities configured secure said implant to said bone.

8. The implant system of claim 1, wherein when viewed from a plane above said load bearing surface, said implant includes a front section, a rear section, and two lateral sections extending along said length between the front and rear sections, the implant further including a "D" shaped cross-section in which one of the lateral sections has a curved profile generally corresponding to at least a portion of a lateral edge of said tibial plateau of said tibial bone.

9. The implant system of claim 1, wherein said implant comprises an upper portion configured to be secured to a lower portion, said upper portion comprising said load bearing surface and said lower portion comprising said bone facing surface.

10. The implant system of claim 1, wherein said implant is a unitary component.

11. The implant system of claim 10, wherein said implant is made from ultra-high molecular weight polyethylene.

12. The implant system of claim 1, wherein said load bearing surface has a concaved contour.

13. The implant system of claim 12, wherein said implant has a height along a first side which is less than a height of a second side.

14. The implant system of claim 13, wherein said first side configured to be located adjacent a medial side of said tibial bone and said second side configured to be located adjacent a lateral side of said tibial bone.

15. The implant system of claim 1, wherein said first and said second truncated cylindrical protrusion generally extend along an anterior to posterior plane.

16. The implant system of claim 15, wherein said implant includes a modified "D" shaped cross-section including a notched region configured to correspond to the posterior face of the tibial bone which is not removed proximate to a nerve bundle.

17. The implant system of claim 1, further comprising a third truncated cylindrical protrusion along said length of said bone facing surface, said third truncated cylindrical protrusion partially overlapping said first and said second truncated cylindrical protrusions and being defined by a third truncated cylindrical projection different than said first and said second truncated cylindrical projections.

18. The implant system of claim 1, further comprising a guide configured to be coupled generally perpendicular to said bone proximate to said defect, said guide comprising a body portion defining a first and a second excision passageway, said first and said second excision passageway each defining a generally cylindrical core pathway configured to extend generally perpendicular to said tibial bone, wherein projections associated with said first and said second generally cylindrical core pathways corresponds to said first and said second different truncated cylindrical projections and are adapted to define a first and a second truncated cylindrical excision site extending through a portion of said articular surface.

19. The implant system of claim 1, wherein when viewed from a plane above said load bearing surface, said implant includes a front section and a rear section, and two lateral sections extending along said length between the front and rear sections, wherein one of the lateral sections has a curved profile generally corresponding to at least a portion of a lateral edge of said tibial plateau of said tibial bone.

20. An implant system comprising an implant for replacing only a portion of a patient's articular surface of a tibial plateau of a tibial bone, said implant including:
  a load bearing surface having a contour based on a plurality of measurements taken of the removed portion of the articular surface corresponding to an implant site in the tibial plateau of the tibial bone; and
  a bone facing surface including a first and a second truncated cylindrical protrusion extending along a length of said bone facing surface and defining a first and a second generally opposite lateral side of said bone facing surface, said first and said second truncated cylindrical protrusion comprising arcs of circles and are defined by portions of a first and a second different cylindrical projection corresponding to said arcs of said circles;
  wherein said implant includes a "D" shaped cross-section and has a thickness extending between said load bearing surface and said bone facing surface that is less than a diameter of said circles and is configured such that the bone facing surface abuts against the tibial bone within the implant site and the load bearing surface is substantially continuous with the articular surface surrounding the removed portion of articular surface when the implant is received in the implant site; and
  wherein portions of the load bearing surface opposite the bone facing surface of said first and said second truncated cylindrical protrusion are disposed within said first and said second different cylindrical projection.

21. An implant system comprising an implant for replacing only a portion of a patient's articular surface of a patient's tibia bone, said implant including:
  a load bearing surface having a contour substantially corresponding to a contour of only the removed portion of the articular surface corresponding to an implant site in the bone; and
  a bone facing surface including a first and a second truncated cylindrical protrusion from said load bearing surface along a length of said bone facing surface and defining a first and a second generally opposite lateral side of said bone facing surface, respectively, said first and said second truncated cylindrical protrusion comprising arcs of circles and are defined by portions of a first and a second different cylindrical projection corresponding to said arcs of said circles;
  wherein said implant includes a modified "D" shaped cross-section including a notched region corresponding to the posterior face of the tibia bone which is not removed proximate to a nerve bundle and the implant has a thickness extending between said load bearing surface and said bone facing surface that is less than a diameter of said circles and is configured such that the bone facing surface abuts against the bone within the implant site and the load bearing surface is substantially continuous with the articular surface surrounding the removed portion of articular surface when the implant is received in the implant site; and wherein portions of the load bearing surface opposite the bone facing surface of said first and said second truncated cylindrical protrusion are disposed within said first and said second different cylindrical projection.

* * * * *

UNITED STATES PATENT AND TRADEMARK OFFICE
CERTIFICATE OF CORRECTION

PATENT NO. : 10,624,752 B2  
APPLICATION NO. : 14/133943  
DATED : April 21, 2020  
INVENTOR(S) : George Sikora et al.

Page 1 of 1

It is certified that error appears in the above-identified patent and that said Letters Patent is hereby corrected as shown below:

On the Title Page

Item (60), in Column 1, Line 2 of the Related U.S. Application Data, delete "which is" and insert -- and --, therefor.

Signed and Sealed this  
Fourteenth Day of July, 2020

Andrei Iancu  
*Director of the United States Patent and Trademark Office*